(12) United States Patent
Ghanavi

(10) Patent No.: US 8,663,675 B2
(45) Date of Patent: Mar. 4, 2014

(54) INJECTABLE MATRIX HAVING A POLYMER AND A STEM CELL NICHE COMPOSED OF CUP-SHAPED NANOPARTICLES CONTAINING GROWTH FACTORS OR PHYSIOLOGICAL AGENTS FOR ORGAN RECONSTRUCTION

(76) Inventor: Jalaledin Ghanavi, Tehran (IR)

( * ) Notice: Subject to any disclaimer, the term of this patent is extended or adjusted under 35 U.S.C. 154(b) by 512 days.

(21) Appl. No.: 12/948,918

(22) Filed: Nov. 18, 2010

(65) Prior Publication Data

US 2011/0064810 A1    Mar. 17, 2011

(51) Int. Cl.
*A61F 13/00*    (2006.01)
*A61F 2/00*     (2006.01)
*C07K 14/47*    (2006.01)
*A61K 38/18*    (2006.01)

(52) U.S. Cl.
USPC ............ 424/422; 514/7.6; 514/965; 424/425; 977/705

(58) Field of Classification Search
None
See application file for complete search history.

(56) References Cited

PUBLICATIONS

Kobel et al. High-throughput methods to define complex stem cell niches. Biotechnique (Focus on Cell Culture Technology), 2010, vol. 48, pp. ix-xxii, doi 10.2144/000113401.*

* cited by examiner

*Primary Examiner* — Deborah Crouch
(74) *Attorney, Agent, or Firm* — Barry Choobin; Patent 360 LLC

(57) ABSTRACT

The various embodiments herein relate to an injectable matrix used for regeneration, reconstruction, repair or replacement of organ or tissue. The injectable matrix consists of a synthetic and natural polymer, a stem cell niche and nanoparticles in the form of cups filled with growth factor and physiologic agent. The embodiments herein also provide a method for regeneration, reconstruction, repair or replacement of organ or tissue. In the method, an injectable matrix is injected to create three dimensional matrix system or network in an area of the desired tissue or organ, migration of blood circulatory stem cells or tissue-specific progenitor cells occur to the injected area of the tissue or organ. The growth factors and physiological agent present in the nanocups are released. The stem cells proliferate and differentiate to form the desired organ or tissue.

22 Claims, 18 Drawing Sheets

INJECTABLE MATRIX HAVING A POLYMER AND A STEM CELL NICHE COMPOSED OF CUP-SHAPED NANOPARTICLES CONTAINING GROWTH FACTORS OR PHYSIOLOGICAL AGENTS FOR ORGAN RECONSTRUCTION

BACKGROUND

1. Technical Field

The embodiments herein generally relate to the field of tissue engineering and particularly to tissue regeneration, reconstruction, repair, augmentation and replacement. The embodiments herein more particularly relate to a method for regeneration, reconstruction, repair, augmentation and replacement of organs or tissue structures. The embodiments herein also relate to bio-absorbable and biocompatible injectable matrixes for regeneration, reconstruction, repair, augmentation or replacement of organs or tissue structures shaped to conform to at least a part of organs or tissues. Moreover, the embodiments herein also relate to materials for bio-absorbable and biocompatible injectable matrixes.

2. Description of the Related Art

Tissue engineering has emerged as a multi-disciplinary field which combines biology, materials science and surgical reconstruction. Tissue engineering provides living tissue products which can be restored and maintained in order to provide improved tissue function. The need for this approach has arisen primarily due to the lack of donor organs and tissues. Tissue engineering offers a promise of being able to dramatically expand the ability to repair tissues and develop improved surgical procedures. In general, there are three distinct approaches which are currently being used to engineer new tissues. They are: firstly, infusion of isolated cells or cell substitutes, secondly, use of tissue inducing materials and/or tissue regeneration scaffolds (sometimes referred to as guided tissue repair) and thirdly, implantation of cells seeded in scaffolds (either prior to or subsequent to implantation). In the third case, the scaffolds may be configured either in a closed manner to protect the implanted cells from the body's immune system or in an open manner so that the new cells can be incorporated into the body.

In open scaffold systems and guided tissue repairs, tissue engineering devices have normally been fabricated from natural protein polymers such as collagen, chitosan or from the synthetic polymers such as the FDA approved materials including polyglycolic acid (PGA), polylactic acid (PLA), polyglactin 910 (comprising a 9:1 ratio of glycolide per lactide unit known as VICRYL™), polyglyconate (comprising a 9:1 ratio of glycolide per trimethylene carbonate unit known as MAXON™) and polydioxanone (PDS). The natural protein polymers and the synthetic polymers degrade over time in both the cases and are replaced by new tissue. While some of these materials have proved to be good substrates for cell and tissue growth and provide good scaffolding to guide and organize the regeneration of certain tissues. But still they often do not have the specific mechanical requirements that a scaffold should have until a new tissue is developed and is able to take over its functions. Also, these materials are sometimes difficult to process and fabricate into the desired form or are handled poorly in the operating room. At times, they are difficult to suture and fall apart prematurely. For example, it has been reported that tissue engineered heart valve leaflet scaffolds derived from polyglactin and PGA are too stiff and had caused severe pulmonary stenosis when implanted in sheep (Shinoka, et al., "New frontiers in tissue engineering: tissue engineered heart valves" in Synthetic Bioabsorbable Polymer Scaffolds (Atala & Mooney, eds.) pp. 187-98 (Birkhäuser, Boston, 1997)).

Attempts have been made to develop new bio-absorbable and biocompatible polymers with more flexible and elastomeric properties. Among them one approach is to incorporate lactide or glycolide and caprolactone joined by a lysine-based di-isocyante into a polyurethane (Lamba, et al., "Degradation of polyurethanes" in Polyurethanes in Biomedical Applications, pp. 199-200 (CRC Press LLC, Boca Raton, Fla., 1998). However, these cross-linked polyurethane networks cannot be processed by standard techniques such as solution casting or melt processing thus limiting their usefulness. Also, there is no evidence that these polyurethane segments are completely biodegraded in vivo. A commercial material, known as TONE™ has also been evaluated as an elastomeric implant material. But, this material degrades very slowly in vivo and thus has a limited application (Perrin, et al., "Polycaprolactone" in Handbook of Bioabsorbable Polymers (Domb, et al., eds.) pp. 63-76 (Harwood, Amsterdam, 1997)). Another approach to synthesize protein-based polymers particularly the polymers containing elastomeric polypeptide sequences has been there (Wong, et al., "Synthesis and properties of bioabsorbable polymers used as synthetic matrices for tissue engineering" in Synthetic Bioabsorbable Polymer Scaffolds (Atala & Mooney, eds.) pp. 51-82 (Birkhäuser, Boston, 1997). But is not reported to biodegrade in vivo although the cells can invade matrices derived from these materials. They also lack the advantages of thermoplastic polymers in fabrication of devices.

U.S. Pat. Nos. 5,468,253 and 5,713,920 both to Bezwada et al., disclose bio-absorbable elastomeric materials which are used to form devices and are alleged to get completely bio-absorbed within a year or six months according to the in vitro data. However, deGroot et al., Biomaterials, 18:613-22 (1997) provides in vivo data for these materials and reports that the implanted material fragmented after 56 weeks into white crystalline-like fragments. It is suspected that these fragments are crystalline poly-L-lactide which degrades slowly. Nonetheless, whatever the composition of the fragments be the material is not completely bio-absorbed even after one year in vivo. These materials are also difficult to process and may have poor shelf stability.

Tissue engineering for regenerative medicine purposes involves the reconstruction of tissue equivalents to replace the physiologic functions of tissues lost due to disease or injury. Tissue engineering requires the use of a cell source to allow for the generation and maintenance of tissue-specific biological functions as well as the use of synthetic or natural injectable matrix materials to support and guide tissue development. Engineering a complex organ such as lung, liver, kidney, heart or small intestine presents so many scientific challenges that development of clinically applicable replacement tissues has not yet been realized. Problems to be faced in the development of any complex tissue, including lung, depend on the following: the development of better systems to promote angiogenesis, the selection of appropriate cell sources, the reproducible differentiation of the selected cell type or types along organ-specific lineages and the development of appropriate scaffolds or matrices to enhance and support three-dimensional (3D) production of tissues. Because complex organs such as the lung involve more than one cell type, an understanding of the factors involved in the differentiation potential of the selected cell source is invaluable. A major problem in engineering of any tissues for clinical application is selecting human cell sources with the potential to provide sufficient number of cells for development of tissue used to repair critical defects caused by disease or injury beyond the repair capabilities of the human body.

A preferred fabricated form of the composition is a porous (fibrous) construct particularly the ones which can be used as tissue engineering scaffolds and guided tissue repair meshes and matrices. This construct or matrix can be derived by any suitable method including salt leaching, sublimation, solvent evaporation, spray drying, foaming and processing of the materials into fibers and subsequent processing into woven or non-woven devices. Such constructs can be used in tissue engineering applications for the tissues of the cardiovascular, gastrointestinal, kidney, genitourinary, musculoskeletal and nervous system as well as for those of the oral, dental, periodontal and skin tissues. Examples of such constructs can be used to prepare tissue engineering scaffolds for both hard and soft tissues. Representative tissue types include, but are not limited to, cardiovascular (including blood vessel, artery and heart valve), cornea and other ocular tissues, pancreas, alimentary tract (e.g. esophagus and intestine), ureter, bladder, skin, cartilage, dental, gingival tissue, bone, liver, kidney, genital organs (including penis, urethra, vagina, uterus, clitoris and testis), nerve, spinal cord, meniscus, pericardium, muscle (e.g. skeletal), tendon, ligament, trachea, phalanges and small joints, fetal and breast.

In general, there is a worldwide shortage of healthy organs for transplant particularly the epithelial-derived organs such as the liver, pancreas, thyroid and pituitary. For example, a shortage of livers exists for orthotopic organ transplant, as a source of primary hepatocytes for clinical therapies to treat acute and chronic liver failure and for extracorporeal liver assist devices. Attempts to propagate primary human hepatocytes in culture have met with limited success because adult human hepatocytes, unlike newborn-derived hepatocytes, do not have a high proliferative capacity. Another strategy is to use primary porcine hepatocytes or organs for transplants.

Bioresorbable scaffolds are the materials that can be broken down by the body and do not require mechanical removal. Bioresorbable scaffolds may be used as a temporary scaffolding for transplanted cells and thereby allow the cells to secrete extracellular matrix of their own to enable, in the long term, a complete and natural tissue replacement. The macromolecular structure of these scaffolds is selected so that they are completely degradable and are eliminated after they have achieved their function of providing the initial artificial support for the newly transplanted cells. To be useful in cell transplantations, these scaffolds must be highly porous with large surface/volume ratios to accommodate a large number of cells. The scaffolds must be biocompatible, non-toxic to the cells that they carry and to the host tissue into which they are transplanted. The scaffolds must be capable of promoting cellular interactions, promoting the cells to secrete their own extracellular matrix (ECM) components and allowing the retention of the differentiated function of attached cells.

Polysaccharide matrices, such as for example, alginate scaffolds, have been found to be superior to other scaffolds known in the art such as collagen scaffolds in promoting polarized cell-cell and cell-matrix interactions in cultured hepatocytes. They provide adequate sites for the attachment and growth of a sufficient cell mass to survive and function both in vitro and in vivo; support thick layers of cells, such as cell aggregates; and are capable of maintaining the cells in an active functional state before and after implantation/transplantation into a host tissue, at that time the polysaccharide injectable matrix will also become amenable to vascularization from the surrounding tissue. Polysaccharide matrices do not suffer from the drawback of limiting the survival and growth of the cells adjacent to the injectable matrix surface as the cells increase in number within the injectable matrix. Another advantage of polysaccharide matrices is that they are biodegradable but degrade only slowly in vivo and thereby permit the cells carried thereby to be established and to form their own tissue matrix at the site of transplant up to the point where they no longer require the polysaccharide injectable matrix.

Among the various materials used as medical materials, animal collagen has excellent bio-affinity and histo-compatibility. It has low antigenicity and has the action of promoting host cell differentiation and growth. It has a hemostatic action and is completely degraded and absorbed in the body. Consequently, it has properties that are particularly suitable for use as a medical material. At present, animal collagen types I to XIX have been discovered. Collagen type I to V have been used in a variety of ways as medical materials. In particular, type I collagen, useful as an extracellular injectable matrix is most commonly used. These collagens are extracted and purified from the connective tissue of various organs such as skin, bone, cartilage, tendon and viscus of animals such as cows, pigs, birds, kangaroos and so forth by acidic solubilization, alkaline solubilization, neutral solubilization and enzymatic solubilization. In addition, these extracted collagens may be used as thread for medical treatment.

Further, after a cross-linking treatment using a cross-linking agent or to physical cross-linking treatment using radiation, electron beam, ultraviolet rays on the collagen materials, there was hardly any increase in the physical properties of the collagen material, particularly the tear strength. It was not possible to process this material for use as a medical material requiring suturing. Moreover, when a cross-linking agent such as glutaraldehyde or epoxy was used, the toxicity of the cross-linking agent on the body became a problem. Also, there is a disadvantage with the collagen in the biochemical properties, i.e., after using the collagen material the promotional effects on cell growth is lost. In addition, in the case of physical cross-linking treatment, the cross-linking rate is unstable and providing adequate physical properties to the collagen material is also not possible. Also, it has been difficult to perform a cross-linking treatment in order to control the absorption rate of the collagen in the body.

For these reasons, a need has arisen for the development of a collagen material that possesses physical properties that allow suturing still maintaining the biochemical properties inherently possessed by collagen, retain the shape for a certain amount of time even after application to the body. The process of production of the medical material for the desired organ, for examples, an artificial tube for nerve, an artificial tube for spinal cord, an artificial esophagus, an artificial trachea, an artificial blood vessel, an artificial valve or alternative medical membranes such as artificial endo-cranium, artificial ligament, artificial tendons, surgical sutures, surgical prostheses, surgical reinforcement, wound protecting materials, artificial skin and artificial cornea. In particular, there has arisen a strong need in the clinical setting for the development of various types of medical materials that can be used as alternative medical membranes which present no ethical problems, are in stable supply, prevent adhesion of the surgical wound following surgery after being applied to the body, have no risk of infection, do not cause tissue degeneration, allow control of the rate of degradation following application, and have an action that promotes regeneration of biomembranes, especially endocranium, pericardium, pleura, peritoneum or serous membrane.

Regenerative medicine offers new tools to tackle the difficulty for the disorders for which there is currently no good therapeutic option. The trachea is an ideal organ to explore the clinical potential of tissue engineering because severe large airway diseases have been poorly managed by conventional treatments. The success of a graft is determined only by its ability to conduct air lifelong and become a sustainable biological conduit.

In recent years, accidental trauma, accompanying the progress made in anesthesia control and post-operative control, including operative procedure for malignant tumors of organs in the cervical and thoracic parts, there has been an increase in the number of occasions in which it is necessary to reconstitute the trachea or tracheal bifurcation. Although the most clinically reliable reconstruction methods are direct anastomoses such as end-to-end anastomosis and end-to-side anastomosis. These methods are subject to their own restrictions on the range of reconstruction and even within the allowed range. High-degree anastomotic techniques and relaxation sutures etc. are required. Consequently, these procedures tend to be associated with extensive invasion. At that time, the use of a trachea substitute made of an artificial material (hereinafter to be referred to as an "bioartificial trachea") enables reconstruction to be performed easily. As a result, the indications for this operation can naturally be expected to be expanded. Attempts in applying such a bioartificial trachea began with animal experiments conducted by Daniel, R A Jr. (published in J. Thorac. Surg. 17, 335 (1948) "The Regeneration of Defects of the Trachea and Bronchi") and although various attempts have been made using various materials since that time but still no artificial materials that can be sued safely in the clinical application have been developed with the exception of partial prosthesis of the cervical trachea.

In case of bioartificial trachea meant for the intra-thoracic trachea there is the greatest desire for clinical effectiveness, since the bioartificial trachea is subjected to poor conditions like little support and external force. In addition to these common problems, bioartificial trachea requires adequate support, rapid and reliable incorporation in the body with little inflammatory reaction. The countermeasure against leakage of air constitutes the most serious problem.

It is still a great challenge for the surgeons all over the world to reconstruct long-segment defect of the trachea. The best way to resolve this dilemma is tracheal transplantation and artificial prosthesis. However, all the efforts are in vain. Lack of blood supply and rejection hindered transplantation, compatibility with recipients' tissues and not covering with endothelium made all artificial prosthesis only a "stent".

Bioartificial tracheal prosthesis up to now is a big challenge to entire surgical field all over the world. All kinds of prosthesis used previously are like "inner stent" which cannot be integrated with native trachea. Actually, there is an interface between smooth surface of the prosthesis and living tissue, the inner side of which is not covered with living membrane. Therefore, there is always a chance of infection around the prosthesis.

Tissue engineering for regenerative medicine purposes is the reconstruction of tissue equivalents to replace the physiologic functions of tissues lost due to disease or injury. Tissue engineering requires the use of a cell source to allow for the generation and maintenance of tissue-specific biological functions as well as the use of synthetic or natural injectable matrix materials to support and guide tissue development. Engineering a complex organ such as lung, liver, kidney, heart or small intestine presents so many scientific challenges. The development of clinically applicable replacement tissues has not yet been realized.

Problems to be faced in the development of any complex tissue, including lung, depend on: development of better systems to promote angiogenesis, selection of appropriate cell sources, reproducible differentiation of the selected cell type or types along organ-specific lineages and development of appropriate scaffolds or matrices to enhance and support three-dimensional (3D) production of tissues. Because complex organs such as the lung involve more than one cell type, an understanding of the factors involved in the differentiation potential of the selected cell source is invaluable. A major problem in engineering of any tissues for clinical application is selecting human cell sources with the potential to provide sufficient numbers of cells for development of tissue used to repair critical defects caused by disease or injury beyond the repair capabilities of the human body.

Tracheal defects may occur after trauma or prolonged intubation. Resection of tracheal tumors also poses a major challenge for substitution. In an effort to solve this problem, different techniques have been tried but with little success. The various tracheal substitutes and techniques of reconstruction were analyzed by Grillo, who classified them in five categories: foreign materials, nonviable tissues, autogenous tissues, tissue engineering and tracheal transplantation. But attempts with foreign materials have led to certain problems such as chronic infection, airway obstruction and migration of the prosthesis, erosion of major blood vessels and proliferation of granulation tissue. Also, implantation of nonviable tissues either chemically treated, frozen or lyophilized have been associated with poor functional results. Complex procedures involving reconstruction with autogenous tissues such as skin, fascia lata, pericardium, costal cartilage, bladder, esophagus or bowel have been associated with disappointing results. More recently, efforts have been made to induce the formation of cartilaginous tubes covered with epithelial cells, but to date this type of tissue engineering has not provided reliable results. Moreover, tracheal allo-transplantation has also been disappointing due to complication of necrosis or stenosis of the graft. In addition immunosuppressive therapy does not permit a clinical application in the treatment of cancer. Recently, Martinod and colleges have used autogenic aortic graft and allogenic aortic grafts to replace long segments of tracheal defect and carina using sheep as animal model with promising results. Seguin and colleges have used cryopreserved, decellularized aortic allograft supported by temporary stent to prevent airway collapse.

Thus, while the current bio-absorbable and bio-compatible polymers offer a wide range of useful properties for certain medical applications. It is desirable to develop methods to prepare bio-absorbable and biocompatible polymers that significantly extend the range of properties available. It would thus be desirable to develop methods for preparing bioabsorbable and biocompatible polymers with mechanical properties closer to those of tissue, particularly for soft tissues. It would also be desirable to develop methods for making bioabsorbable biocompatible materials which can be readily processed and fabricated into tissue engineering devices that can be easily implanted. The embodiments herein define the component parts of tissue engineering and review the experimental methods used to produce airway implants to date, including a recent successful, first-in-man experience.

The above mentioned shortcomings, disadvantages and problems are addressed herein and which will be understood by reading and studying the following specification.

OBJECTIVES OF THE EMBODIMENTS

The primary object of the embodiments herein is to provide an injectable matrix adapted for regeneration, reconstruction, repair or replacement of organs or tissue structures having specific mechanical requirements that a scaffold should have until a new tissue is developed and is able to take over its functions.

Another object of the embodiments herein is to provide an injectable matrix which is easily processed into a desired form, easily handled in the operating room and provided with good shelf stability.

Yet another object of the embodiments herein is to provide an injectable matrix with large surface/volume ratios to accommodate a large number of cells.

Yet another object of the embodiments herein is to provide an injectable matrix having an excellent bio-affinity and histo-compatibility.

Yet another object of the embodiments herein is to provide an injectable matrix which is biocompatible and is non-toxic to the cells.

Yet another object of the embodiments herein is to provide an injectable matrix which has low antigenicity and has the action of promoting host cell differentiation and growth.

Yet another object of the embodiments herein is to provide an injectable matrix which has a hemostatic action and is completely degraded and absorbed in the body.

Yet another object of the embodiments herein is to provide an injectable matrix to cause an immigration of blood circulatory stem cells or tissue-specific progenitor cells into damaged organ or tissue.

Yet another object of the embodiments herein is to provide an injectable matrix to enable a migration of blood circulatory stem cells or tissue-specific progenitor cells to target tissues or organs in which a stem cell niche is attached to a scaffold to enable a slow-release of growth factors and other physiologic agents from cup-shaped nanoparticles.

Yet another object of the embodiments herein is to provide an injectable matrix to enable a differentiation of the blood circulatory stem cells or tissue-specific progenitor cells based on an affinity of stem cell niches, growth factor or other physiological agents that are released from cup-shaped nanoparticles (nanocup).

Yet another object of the embodiments herein is to provide an injectable matrix to differentiate a mechanical condition and/or an electrical condition of the cells based on (i) a function of desirable (target) tissue or organ, (ii) connection of desirable tissue or organ with other adjacent organs or tissues and (iii) traction forces (shear stress) of the injectable matrix in damaged desirable (target) tissue or organ to enable the differentiation of stem cells into specialized and desirable (target) tissue or organ.

Yet another object of the embodiments herein is to provide an injectable matrix to demonstrate the role of mechanosensitivity forces in the differentiation of stem cell.

Yet another object of the embodiments herein is to provide an injectable matrix which is capable of promoting cellular interactions, provoking the cells to secrete their own extracellular matrix (ECM) components and allowing the retention of the differentiated function of the attached cells.

Yet another object of the embodiments herein is to provide an injectable matrix so that the injectable matrix presents no ethical problems, enables stable supply, eliminates risk of infection, prevents tissue degeneration and allows controlling of the rate of degradation following an application.

Yet another object of the embodiments herein is to provide an injectable matrix to enable a reconstruction of a defective long-segment in the trachea.

Yet another object of the embodiments herein is to provide a method for regeneration, reconstruction, repair or replacement of organs or tissue structures using the injectable matrix.

Yet another object of the embodiments herein is to provide a method for a successful transplantation of bioartificial trachea with no rejection, no infection, no surgery and even no major complications.

Yet another object of the embodiments herein is to provide a method of transplantation or tissue engineering which is simple and efficient.

These and other objects and advantages of the embodiments herein will become readily apparent from the following detailed description taken in conjunction with the accompanying drawings.

SUMMARY

The various embodiments herein provide an injectable matrix for regeneration, reconstruction, repair or replacement of organ or tissue. The injectable matrix comprises a polymer, a stem cell niche, cup-shaped nanoparticles, growth factors and other physiologic agents including peptide and steroid hormones. The matrix is in the form of a gel, a paste, a spray, a vapor of nano and micro-particle or liquid or any other injectable form preferably hydrogel form. The polymer is selected from a group comprising of synthetic and natural polymers. The synthetic polymer comprises of at least one of poly-caprolacton, poly-l-lysin, poly-lactic-co-glycolic acid. The natural polymer comprises of at least one of collagen, elastin, chitosan, alginate or combination thereof wherein the collagen comprises of at least one of 29 Types of collagen preferably type I, II, III, IV and V. The polymer herein further comprises of fibronectin, laminin, glycoprotein, elastin, mucopolysaccharide, heparin sulfate, chondroitin sulfate, keratin sulfate, glycosaminoglycan, hyaluronic acid, proteoglycan, polysaccharide and any combination thereof. The cup-shaped nanoparticles have diameter of less than 5 micrometer and particularly within 60 to 1000 nm. The growth factor herein is selected from a group comprising epidermal growth factor (EGF), transforming growth factor alpha (TGF-alpha), transforming growth factor beta (TGF-beta), fibroblast growth factor (FGF) and vascular epithelial growth factor (VEGF), wherein the FGF is selected from bFGF (Basic fibroblast growth factor) group and from a group consisting of FGF2, FGF7, FGF10 and any combination thereof. The physiological agent herein comprises of biologically active molecules such as peptide, steroid hormones, chemokine, cytokine or a combination thereof. The shape of the matrix is to conform at least a part of organ or tissue herein the preferable shape is a circle or a c-shape. The cup-shaped nanoparticles have cross-sectional dimension of less than 1000 nm and particularly less than 100 mm. The organ or tissue in need of comprises structures involving hollow and epithelial organs such as respiratory organ, cardiovascular organ, gastrointestinal organ, lymphatic organ, dental organ, periodontal organ or skin organ preferably trachea.

The embodiments herein provide a method for regeneration, reconstruction, repair or replacement of organ or tissue. The injectable matrix is first injected on or in an area of an organ or tissue in need of. The blood circulatory stem cells or tissue-specific progenitor cells are migrated to the injected area of the organ or tissue. Then, the growth factor and physiological agent present in the cup-shaped nanoparticles are released. The stem cells migrated from the blood circulatory stem cells or tissue-specific progenitor cells proliferate and differentiate to re-construct the complete desired organ or tissue. The number of injections of the injectable matrix is more than one in case of complex organs such as trachea. The injectable matrix herein can be without stem cells. The injectable matrix can be injected in more than one part of the organ.

The embodiments herein relate to methods and materials for tissue reconstruction, repair and replacement. More specifically, the embodiments herein provide for the treatment of patients using an injectable matrix comprising a biocompatible, biodegradable, synthetic or natural polymeric injectable matrix shaped to conform to at least a part of a hollow or epithelial organ or tissue structure. The embodiments herein provide bioabsorbable, biocompatible and injectable polymers for tissue engineering and tissue regeneration in human trachea from these materials.

The embodiments herein describe methods and materials for construction of bio-absorbable and bio-compatible matrix that can be used in reconstruction, repair or replacement of tissues and organs. The matrix is made up of synthetic or natural polymer and has stem cell niches and nanocups. The nanocups are filled with growth factors or other physiological active agents. After the injection of the matrix into the damaged organ or tissue, immigration of tissue-specific progenitor cells and blood circulatory stem cells occur and get attached to the injectable matrix. After the release of growth factors, these stem cells differentiate into desirable target tissue or organ.

The embodiments herein also provide a method of treatment of patients in need thereof using a matrix that includes a biocompatible, biodegradable, synthetic or natural polymeric scaffold which is shaped to conform to at least a part of desired organ or tissue. The matrix has features which are particularly well-suited for structures involving hollow and epithelial organs such as respiratory, cardiovascular, gastrointestinal, lymphatic system and skin. The matrix comprises a synthetic or natural-sourced polymer configured in size and shape to fit the defective site which is to be repaired. The matrix can also be shaped into a number of desirable configurations with multiple injections to satisfy a large number of human organs and organ systems or any other space restrictions. The matrix is made up of synthetic or natural-sourced polymers such as collagen, elastin, chitosan, alginate, poly-caprolacton, poly l-lysine, poly-lactic-co-glycolic acid. The matrix comprises stem cell niche, nanoparticles such as slow-release nanocups carrying growth factors and other physiologic agents. The other physiologic agents include peptide and steroid hormones which help in promoting proliferation and differentiation of the stem cells. The stem cells are derived from blood circulatory stem cells or tissue-specific progenitor cells.

According to one embodiment, the composition of the matrix can be formulated in a gel, a paste, a spray with nano and micro-particles, a liquid or any other injectable form. The preferred form is a hydrogel which is injectable. The matrix is administered to the defect by injection. The number of injections depends on the type and extent of tissue or organ structure damage. The complex organs such as the trachea involve more than one cell type so the number of injections is more than one step. All of the matrix structures such as synthetic or natural polymer, niches, growth factors and other physiologic agents specially depend on the type of desired organ or tissue. The composition of the matrix can assume a variety of configurations. It can comprise a synthetic or natural-sourced injectable matrix configured in size and shape to fit the defect of the site which is to be repaired. The polymeric injectable matrix may be shaped into any number of desirable configurations to satisfy any number of overall systems, geometries or space restrictions. The scaffold can also be modified in vitro before use and can carry growth factors. The injectable matrix can comprise a composition to formulate a gel, paste, a spray with nano and micro-particles, a liquid or any other injectable form. The preferred form is a hydrogel which is injected.

The embodiments herein relate to a method adapted for regeneration, reconstruction, repair or replacement of organs or tissue structures using an injectable matrix. The matrix comprises a synthetic or natural polymer, stem cell niches, nanocups filled with growth factors or other physiological active factors. An injection of the matrix causes immigration of blood circulatory stem cells or tissue-specific progenitor cells into the damaged organ or tissue. The blood circulatory stem cells or stem cells migrated are based on the affinity to stem cell niches and differentiated based on growth factors or other physiological agents released from the cup-shaped nanoparticles (nanocups). These stem cells are differentiated into the desired (target) tissue or organ.

According to one embodiment, the method of treatment of a patient in need thereof includes the steps wherein an injectable matrix is provided or injected in or an area of the organ or tissue structure in need of treatment. The injectable matrix or scaffold made up of biocompatible synthetic or natural polymers joined with stem cell niches and nanoparticles in the shape of cups filled with growth factors and other physiologic agents. The injectable matrix is shaped to conform to at least a part of the organ or tissue structure in need of the treatment. The biocompatible synthetic or natural polymers include collagen, elastin, chitosan, alginate, polycaprolacton, poly l-lysine, poly-lactic-co-glycolic. The growth factors are selected from a group comprising EGF, TGF-alpha TGF-beta, FGF and VEGF, wherein the FGF is selected from bFGF (Basic fibroblast growth factor) group and from a group consisting of FGF2, FGF7, FGF10 and any combination thereof. The physiological agent herein comprises of biologically active molecules such as peptide, steroid hormones, chemokine, cytokine or a combination thereof. The migration of the blood circulatory stem cells or stem cells is derived from tissues or organs (tissue-specific progenitor cells) to the stem cell niches attached to the scaffold. Then the slow-release of growth factors and other physiologic agents from the cup-shaped nanoparticles occurs at the different time of injection based on different layer of cup. Based on these events, the blood circulatory stem cells or stem cells that are derived from tissues or organs are allowed to proliferate and differentiate into the desired organ or tissue.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

DETAILED DESCRIPTION OF THE EMBODIMENTS

Figure 1:
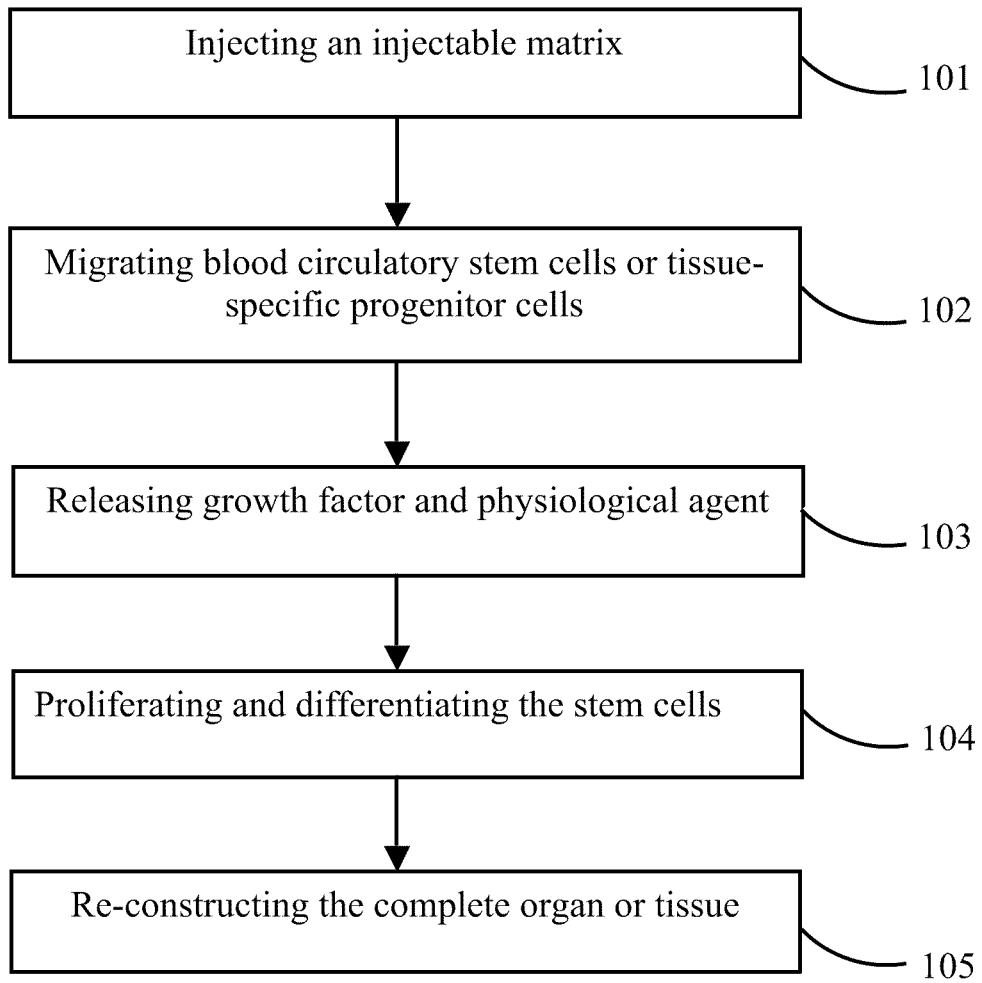
FIG. 1 illustrates a flow chart illustrating the various steps in the method for regeneration, reconstruction, repair or replacement of organ or tissue.
Figure 2:
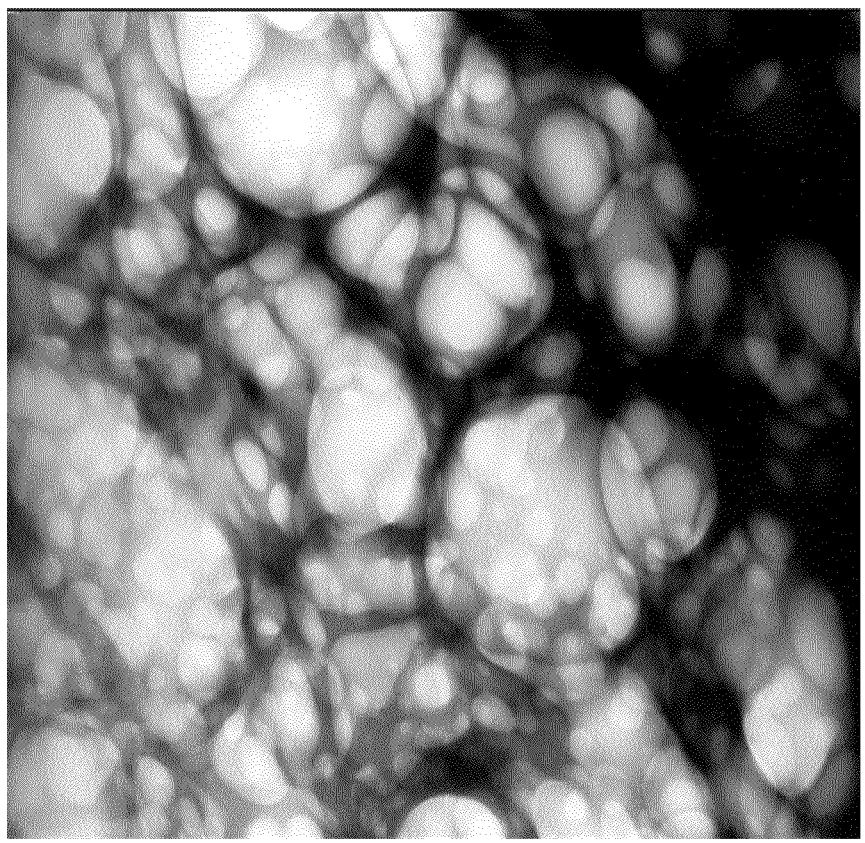
FIG. 2 shows a transmission electron microscopy (TEM) image of injectable matrix comprising collagen, chitosan and nanocup, according to an embodiment herein.

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein describe an expressing markers associated with migration and differentiation of stem cells and an aggregate which assumes a structure or performs a function associated with an epithelial and hollow organ or a fragment thereof. The embodiments herein also provide a method of treating a subject in need of repair or replacement of an organ or a portion thereof; and/or a method of treating a subject with a disease or disorder which impairs or abrogates a trachea, lymphatic vein, lung, liver, kidney or pancreas. Many parameters are required for design and production of matrix, such as, improved biocompatibility and elasticity, development of new niche to promote stem cell migration and adhesion and development of nanoparticles that control release of growth factors as needed during tissue assembly.

According to one embodiment, a method of tissue engineering for organ reconstruction comprising the steps of injecting a matrix on or in an area of an organ or tissue in need of and wherein the injectable matrix includes a polymer, a stem cell niche and cup shaped nano particles. A three dimensional matrix system or network with the injected area of the organ or tissue is created as a whole matrix. A plurality stem cells or tissue-specific progenitor cells is migrated to the three dimensional matrix system or network. Growth factors and physiologic agents are released in the injected area of the organ or tissue. The migrated plurality of stem cells or tissue-specific progenitor cells are proliferated and differentiated along with a mechanical in-vivo stress. Then the organ or tissue is re-constructed.

The injected matrix is in the form of a gel, a paste, a spray, a vapor of nano and micro-particle or liquid or in any other injectable form and wherein the injected matrix is in the form of a hydrogel.

The plurality of stem cells is derived from blood circulatory system and tissue-specific progenitor cells of the organ or tissue. The plurality of stem cells is differentiated based on affinity of the stem cell niche, the growth factors and physiologic agents and mechanical and electrical in-vivo stress. The mechanical and electrical in-vivo stress depends on a function of the tissue or organ, a connection of the tissue or organ with adjacent organs or tissues and traction forces or shear stress base on function of the tissue or organ upon the complex of injectable matrix network and migrated stem cells.

The growth factor is selected from a group comprising of epidermal growth factor (EGF), transforming growth factor alpha (TGF-alpha), transforming growth factor beta (TGF-beta), fibroblast growth factor (FGF) and vascular epithelial growth factor (VEGF), wherein the fibroblast growth factor (FGF) is selected from a group consisting of bFGF, FGF2, FGF7, FGF10 and any combination thereof.

The physiological agent is selected from a group comprising of biologically active molecules and wherein the biologically active molecules include peptides, steroid hormones, chemokines, cytokines or a combination thereof.

The organ or tissue is selected from a group comprising of structures involving hollow and epithelial organs and wherein the hollow and epithelial organs include respiratory organ, cardiovascular organ, gastrointestinal organ, lymphatic organ, dental organ, periodontal organ or skin organ.

The matrix injected into a complex organ is more than one and wherein the complex organ is trachea. The matrix is injected without stem cells. The matrix is injected in to one or more parts of the organ. The injected matrix configures a network of spherical structure in the injected area of the tissue or organ with or without internal or external mechanical support.

According to an embodiment, an injectable matrix for tissue engineering comprising a polymer, a stem cell niche, a cup-shaped nanoparticles, a growth factor and a physiological agent.

The polymer is selected from a group comprising of synthetic polymers and natural polymers. The synthetic polymer is selected from a group comprising of poly-caprolacton, poly-l-lysin, poly-lactic-co-glycolic acid. The natural polymer is selected from a group comprising of collagen, elastin, chitosan, alginate or combination thereof and wherein the collagen includes 29 types of collagen and wherein the preferred type of collagen is I, II, III, IV and V.

The polymer is selected from a group comprising of fibronectin, laminin, glycoprotein, elastin, fibrillin, mucopolysaccharide, heparin sulfate, chondroitin sulfate, keratin sulfate, glycosaminoglycan, hyaluronic acid, proteoglycan, vitronectin, polysaccharide and any combination thereof.

The stem cell niche comprises a specified niche for specific organ wherein the specified niche comprises purified collagen from the organ.

The cup-shaped nanoparticles have diameter of less than 5 micrometer and wherein the cup-shaped nanoparticles have diameter of 60 to 1000 nm.

The growth factor is selected from a group comprising of epidermal growth factor (EGF), transforming growth factor alpha (TGF-alpha), transforming growth factor beta (TGF-beta), fibroblast growth factor (FGF) and vascular epithelial growth factor (VEGF), wherein the fibroblast growth factor (FGF) is selected from a group consisting of bFGF, FGF2, FGF7, FGF10 and any combination thereof.

The physiological agent is selected from a group comprising of biologically active molecules and wherein the biologically active molecules include peptides, steroid hormones, chemokines, cytokines or a combination thereof.

The shape of the matrix is to conform a shape of at least a part of organ or tissue.

FIG. 1 illustrates a flow chart showing the various steps of the method for regeneration, reconstruction, repair or replacement of organ or tissue. With respect to FIG. 1, the injectable matrix is first injected on or in an area of an organ or tissue in need of (101). The blood circulatory stem cells or tissue-specific progenitor cells are migrated to the injected area of the organ or tissue (102). Then, the growth factor and physiological agent present in the cup-shaped nanoparticles are released (103). The stem cells migrated from the blood circulatory stem cells or tissue-specific progenitor cells proliferate and differentiate (104). The cells after proliferating and differentiating re-construct the complete desired organ or tissue (105).

As used herein the term "biocompatible material" is any substance which is not having any toxic or injurious effects on biological functions. As used herein the term "synthetic polymer" refers to polymers that are not found in nature even if the polymers are made from naturally occurring biomaterials. The term "natural polymer" refers to polymers that are naturally occurring. According to the embodiments herein, a variety of materials can be used to fabricate structures herein. Materials used to form structures for tissue engineering and/or organ replacement are biocompatible and biodegradable including synthetic or natural polymer, stem cell niches, nanocups filled with growth factors or other physiological agents. In some embodiments, the term "differentiated" as used herein, refers to cells having a specialized structure or function typical of the cell type found with the target organ. The term "Bio-artificial trachea" as used herein refers to injectable matrix which consist of synthetic or natural polymer, stem cell niches, nanocups which are filled with growth factors or other physiological agents.

The polymeric injectable matrix herein can be shaped into any number of desirable configurations to satisfy any number of overall systems or space restrictions. For example, in the use of the polymeric injectable matrix for tracheal stenosis, the injectable matrix may be shaped to conform to the dimensions and shapes of the whole or a part of trachea after dilatation and lasering of stenosis portion. Injection of multiple matrixes with different volume and depth in target organ or tissue, along with effective mechanical stress, increases the speed of the stem cells differentiation which are derived from blood circulatory stem cell or derived from tissue. This occurs when the stem cells get attached to specific niches of the injected matrix (purified collagen from target organ) and cause the slow release of growth factor from nanocups. These features are particularly well-suited for structures involving hollow and epithelial organs.

The composition or the matrix is administered to the defect by injection. The carrier can include an injectable matrix or a substantially injectable cell-free matrix. The carrier may be a solid (e.g. vapor or particulate), or a gel, a paste, a liquid or can be in any other injectable form. Suitable carriers contain materials that include, but are not limited to, allogenic tissue (e.g., devitalized allogenic or xenogenic tissue), collagen (specially Type I, II, III, IV and Type V), chitosan, chitin, alginate, calcium phosphates (e.g. hydroxyapatite), gelatins, dextrins and polymers comprising of lactic acid, butyric acid, glycolic acid and autologous blood. Injectable matrix in liquid or gel forms are particularly suitable for administration by injection so as to provide the scaffold to a defect locus by injection rather than surgical means.

Also the number, shape and size of particles that are injected to the damaged organ with organ itself allow stem cell migration and deposition both on and in the injectable particle. According to some embodiments herein, structures can be made in the shape of organs including vessels, lung, liver, kidney, pancreas, gut, bladder and urethra.

A variety of materials can be used to fabricate the injectable matrix. Materials used to form matrix for tissue engineering and/or organ replacement may be biocompatible and can include synthetic or natural polymers, inorganic materials, or composites of inorganic materials with polymers. In the description herein concerning the use of appropriate materials to fabricate structures, those of ordinary skill in the art can select materials, techniques, etc. based upon general knowledge of the art and available reference materials concerning certain techniques for fabrication, in combination with the description herein.

The polymers described herein may be prepared by synthetic and/or natural methods. However, the method must provide the desired polymer in a form sufficiently pure for use as an implantable material. The polymer should not contain any undesirable residues or impurities which could elicit an undesirable response in vivo. The polymers may be prepared from any combination of monomeric units. These units must be capable of biodegrading in vivo and non-toxic compounds, which can be excreted or further metabolized. The combination of units in the polymer must also be biocompatible and should not elicit an undesirable biological response upon implantation. The polymer may be biodegraded in vivo by any means including hydrolysis, enzymatic attack and a cell-mediated process or by any other biologically mediated process.

Synthetic and/or natural polymers can also be modified in vitro before use and can carry growth factors and other physiologic agents which promote proliferation and differentiation. The mechanical properties of the polymer are also kept in mind while designing a matrix in order to meet the needs of the particular tissue engineering application. Thus, according to the method described herein for preparing bioabsorbable and biocompatible polymers a combination of the correct ratio of the polymeric units is needed.

With respect to the raw materials for making the matrix, various kinds of collagen can be used, for example, neutral-solubilized collagen, acid-solubilized collagen, alkaline-solubilized collagen and enzyme-solubilized collagen, enzyme-solubilized collagen that has been treated with an enzyme such as pepsin, trypsin, chymotrypsin, papain or pronase is preferable. This is because the telopeptide serving as the antigen group in the collagen molecule is effectively removed thereby eliminating nearly all of its antigenicity. The collagens of extracellular matrices in the target organ are extracted from same organ (in animal or human donor) and from placental and/or amniotic membrane. The extraction is followed by enzymatic procedure that can be used for stem cell niche and causes control or initiation of cell migration and adhesion. Whereas, slow-release nanocups with biologically active molecules such as peptide, steroid hormones, growth factors, chemokine and cytokine lead to cell differentiation, proliferation and stimulation of angiogenesis. The Final concentration of the collagen can be between 20% and 75% dependent on the desired target organ or tissue. There is no particular restriction on the origin of the enzymatic collagen, and in general, type I collagen or mixed type I and type II or type III collagen can be used which are obtained by extraction and purification from the skin, bone, cartilage, tendon, viscera and so forth of human or animals such as cows, pigs, rabbits, sheeps, kangaroos, birds, fishes, etc.

Chitosan (poly-β-1-4-glucosamine) is the highly a de-acetylated form of chitin. This amino polysaccharide is protonated and soluble in mineral or organic acid. The degree of chitosan protonation is related to its solubility. When the chitosan is exposed to a pH below 5.0, the amine groups gets protonated and thus making it soluble in water. At a protonation degree between 45% and 100% the chitosan behaves as amphoteric substance leading to an acceptance and donation of protons. Preferably the chitosan is protonated by exposure to formic acid or glacial acetic acid. The low molecular weight chitosan exhibits interesting biological properties for clinical use and cell culture support. Its antimicrobial activity acts by stimulation of the immune system and in particular, it induces the activation of macrophages. The speed of enzymatic degradation of chitosan after in vivo administration is a function of both, its molecular weight and degree of acetylation. The Final concentration between of chitosan can be 5 and 45% depending on the desirable (target) organ or tissue. Low molecular weight chitosan exhibits interesting biological and anti-microbial properties for in vivo cell culture and support.

Alginate hydrogels are very much attractive for using with cells because of mild gelling conditions, low diffusional barrier for all nutrients and relative biocompatibility. A limitation of alginate hydrogels used with a cellular component is the lack of inherent cell adhesion. That is necessary for cell attachment and long term survival of most mammalian cell systems. Physical properties of alginate hydrogels depend on alginate concentration, specific and concentration of divalent cation. Alginate content in this matrix is 0 to 10% by mass dependent on the desirable (target) organ or tissue.

The applicable polymer concentration or amount of solvent which can be utilized varies from system to system. The amount of polymer depends to a large extent on the solubility of the polymer in a given solvent and the final properties of the desired organ or tissue.

Virtually every tissue of the adult organism maintains a population of putatively slowly-cycling stem cells that maintain homeostasis of the tissue and respond to injury when challenged. The niche includes all cellular and non-cellular components that interact in order to control the adult stem cell and these interactions can often be broken down into one of two major mechanistic categories i.e. physical contact and diffusible factors. Blood circulatory stem cells or stem cells are derived from tissues or organs (tissue-specific progenitor cells) and can be stimulated to differentiate by contact with one or more differentiation physiologic agents, such as forskolin, retinoic acid, Insulin-Like Growth Factor (IGF), Transforming Growth Factor (e.g. TGF-alpha, TGF-3), Tumor Necrosis Factor (TNF), Platelet Derived Growth Factor (PDGF), Fibroblast Growth Factor (FGF), hedgehog, Epidermal Growth Factor (EGF), Granulocyte Macrophage-Colony Stimulating Factor (GM-CSF), Hepatocyte Growth Factor (HGF), somatostatin, Vascular Endothelial Growth Factor (VEGF), Brain-Derived Neurotrophic Factor (BDNF), Thyrotropin Releasing Hormone (TRH), growth hormone, Cyclic Adenosine Monophosphate (Camp), phosphodiesterase inhibitors, somatostatin, adenylate cyclase activators, prostaglandins, Ciliary Neurotrophic Factor (CNTF), neurotrophin 3, neurotrophin 4, interleukins, interferons and glucocorticoid hormone.

In one embodiment herein, the new nanoparticles show unique morphologies as nanocups. The nanocups are effectively used to hold and contain other materials leading to the formation of multi-component hybrid nanoparticles. The development of nano-devices as smart delivery systems to target specific sites and nano-carriers for controlled chemical release and allowing slow and constant release of the active substances. According to the embodiments herein, nanocups or cup-shaped nanoparticles are used for the slow-release of growth factor and physiological agents. Initially, thick portion of the nanocup is designed which is based on the type of target tissue and then thin portion of the nanocup is designed, again based on the type of target tissue and releasing time. Moreover, two or more nanocups, containing a different physiologic agent comprising biologically active molecules such as peptide, steroid hormones, growth factors, chemokine, cytokine or a combination thereof that enable stem cells to grow and/or differentiate to the desirable (target) organs or tissues, can be combined to provide for the release of multiple drugs.

According to the embodiments herein, the structure of cup shaped nanoparticles consist of: a thick portion which increases the capability of macromolecules attachment without or minimum of influence on the entire nanocups portion. The material used for this portion may be made of chitin, chitosan or other synthetic or natural polymers. In specific time, these materials have not destructive effects upon physiological and/or pathological factors in a determined period time. Thin portion which could be fabricated from chitosan or other synthetic or natural polymer. In specific time, these materials have destructive effects upon physiological and/or pathological factors. Generally, based on number of thin layers, the amount of released material from nonocup is estimated. Thereby, the volume of nanocup is not considered as a variable from its surface in the release of their materials. The attachment of every molecule to the outer surface of thicker portion of nanocup occurs without possible changes in nanoscale of the nanocup structure. Based on structure and composition of the target tissue the thicker layer of the nanocup is first designed. Then the thinner side depending on the target tissue, time of releasing, the kind of physiological materials that are present inside the nanocup, physiological and/or pathological factors inside the target tissue or organ.

The thinner side of nanocups are fabricated by layer-by-layer techniques and have a diameter of less than 5 micrometer, particularly 60 to 1000 nm (for example, thickness of coating layer is 1.5 to 2.5 nm). A single physiological agent can be encapsulated within a single nanocup. These nanocups can be filled with physiologic agents/components. According to one embodiment herein, a single physiologic agent can be encapsulated in an individual nanocup. Also, a combination of two or more nanocups that contain different physiological agents (i.e. peptide, steroid hormones, growth factors, chemokine, cytokine, their combination) would enable the stem cells to grow and/or differentiate to desirable target organs or tissues or they may provide the release of multiple drugs. According to the embodiments herein, the nature of the physiologic components can be designed depending on the nature of injection site in the target organ. The outer surface of thick portion of nanocups can be attached to synthetic or natural polymer in the matrix for instance collagen. After injection, growth factor and other physiologic components diffuse from the nanocup into the desirable (target) organs or tissues at a predictable and controllable rate.

Also, incorporating nanoparticles in injectable matrix have various sizes depending on nature and amount of physiologic agents/components, time of release and the nature of injection site in the target organ; for example, these nanoparticles may have a cross-sectional dimension of less than 1000 nm, less than 100 nm, less than 50 nm. Nanocup can be filled with physiologic agent based on: property of injection site in target organ, property of the physiologic agent, surface, number and size of nanocups. After injection, physiologic agent can be diffuse from the nanocup into desirable (target) organs or tissues with a predictable and controllable rate. The surface of nanocups in the injectable matrix can be attached with synthetic or natural polymer such as collagen or polycaprolacton.

Figure 3:
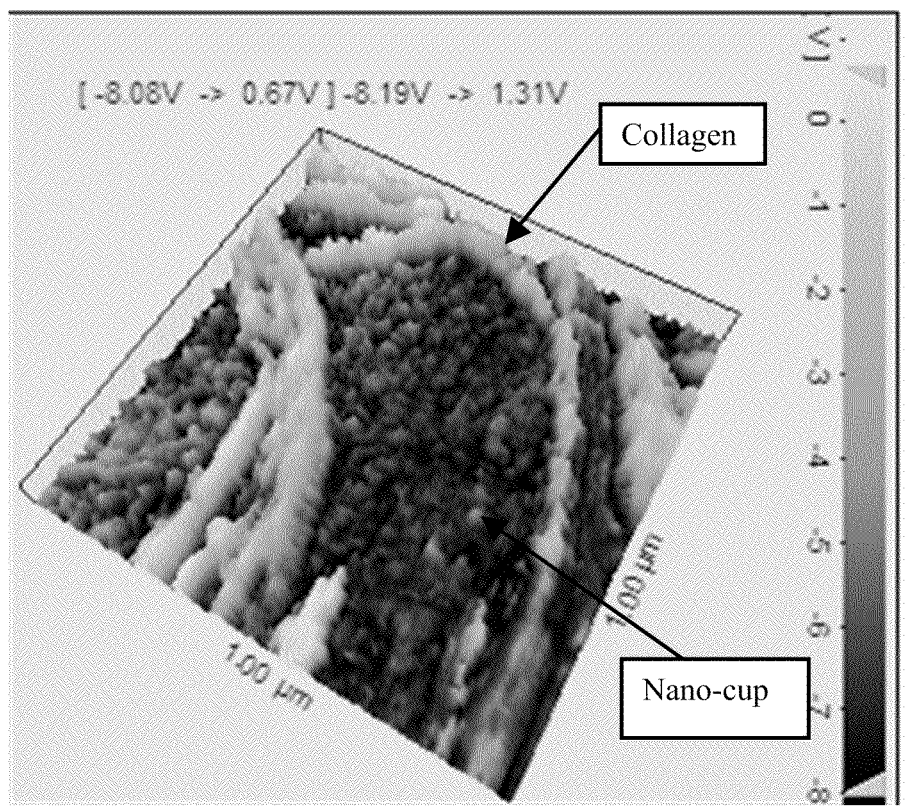
FIG. 3 shows an atomic force microscopy (AFM) image of injectable matrix comprising collagen, chitosan and nanocup, according to an embodiment herein.
Figure 4:
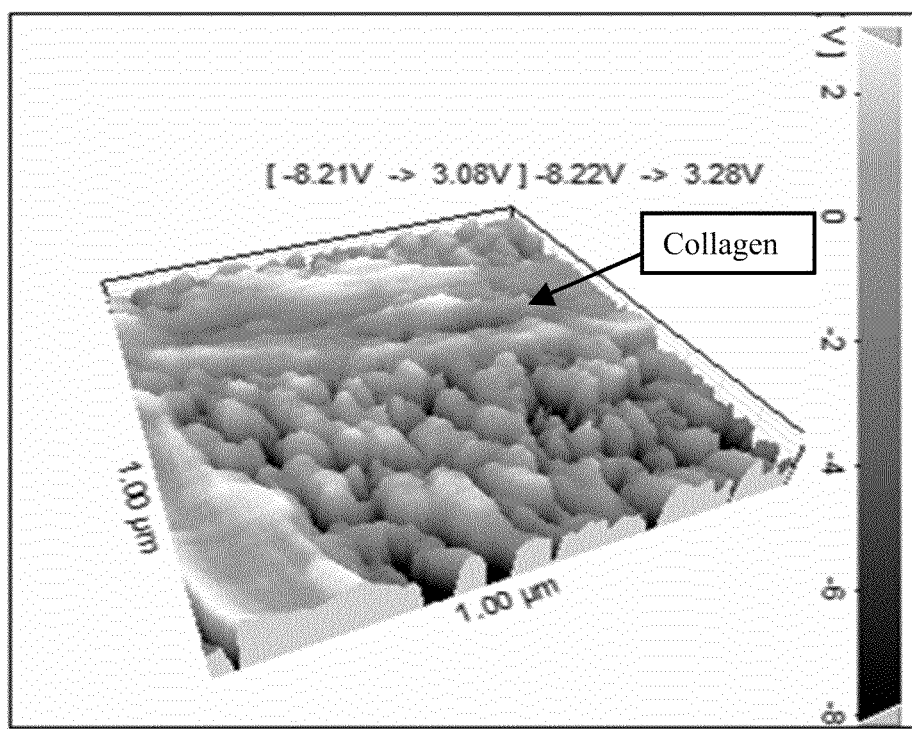
FIG. 4 shows an atomic force microscopy (AFM) image of injectable matrix comprising collagen, chitosan and nanocup, according to an embodiment herein.
Figure 5:
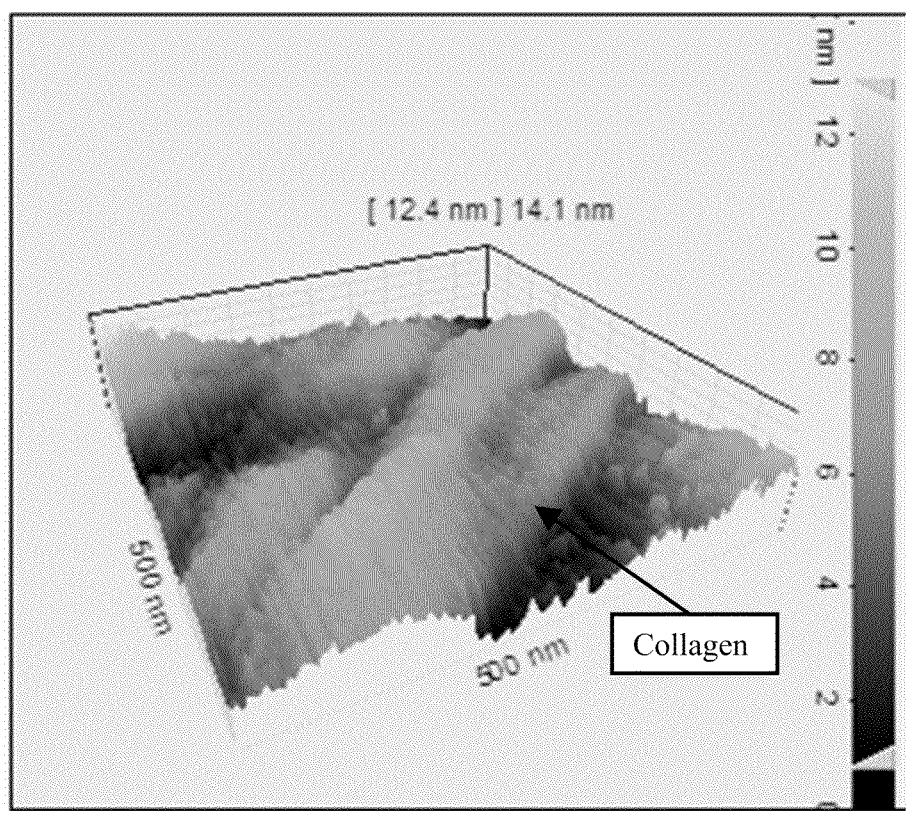
FIG. 5 shows an atomic force microscopy (AFM) image of injectable matrix comprising collagen, chitosan and nanocup, according to an embodiment herein.

FIG. 3 shows an atomic force microscopy (AFM) image of injectable matrix comprising collagen, chitosan and nanocup. With respect to FIG. 3 the nanocups are shown with variable sizes. The collagen injectable matrix can also be clearly seen.

Figure 6:
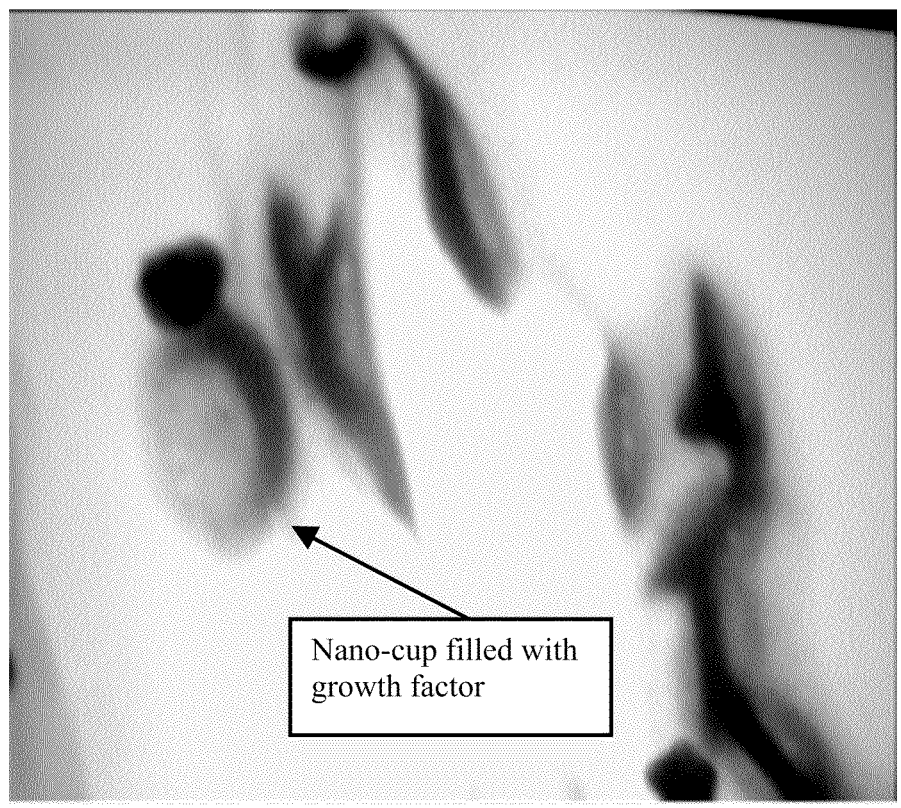
FIG. 6 shows a transmission electron microscopy (TEM) image of nanocup with/or without growth factor according to an embodiment herein.

FIG. 6 shows a transmission electron microscopy (TEM) image of nanocup with/or without growth factor. With respect to FIG. 6, nanocup filled with growth factor can be clearly seen.

Figure 7A:
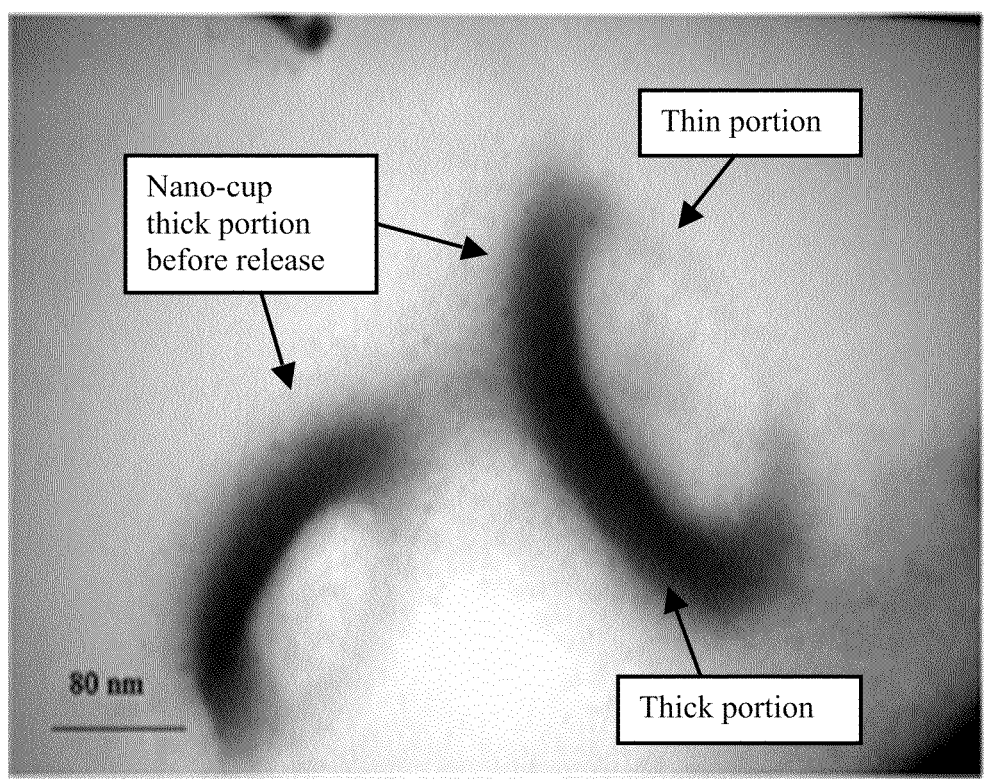
FIG. 7A shows a transmission electron microscopy (TEM) image of a nanocup with/or without growth factor, according to an embodiment herein.

FIG. 7A shows a transmission electron microscopy (TEM) image of a nanocup with/or without growth factor. With respect to FIG. 7A, the thick portion and the thin portion of the nano-cups can also be seen.

Figure 7B:
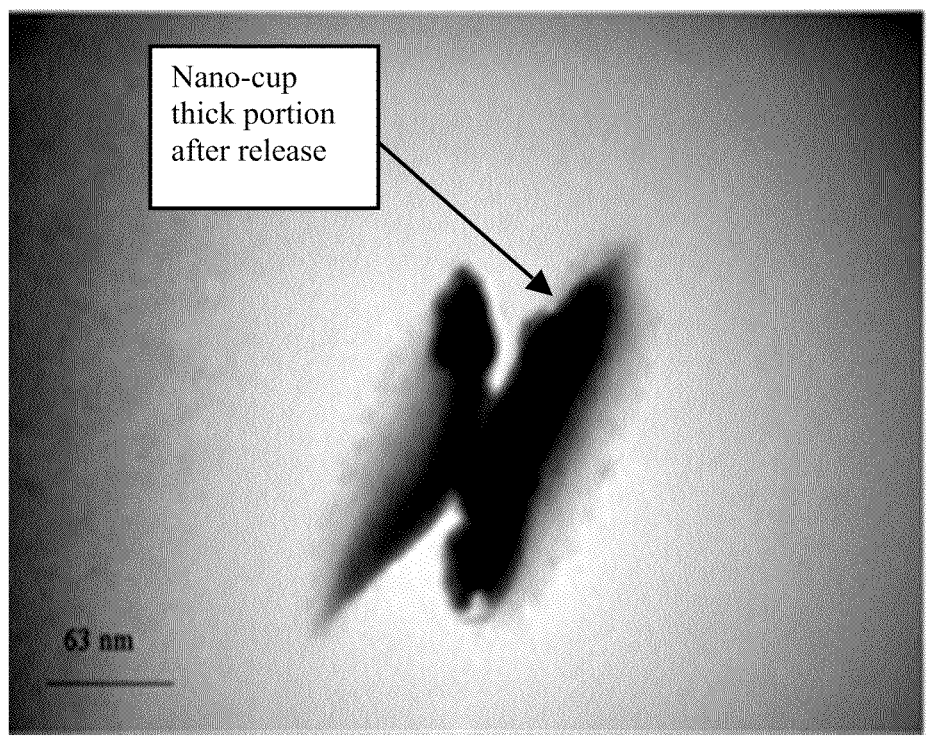
FIG. 7B shows a transmission electron microscopy (TEM) image of a nanocup with/or without growth factor, according to an embodiment herein.
Figure 8:
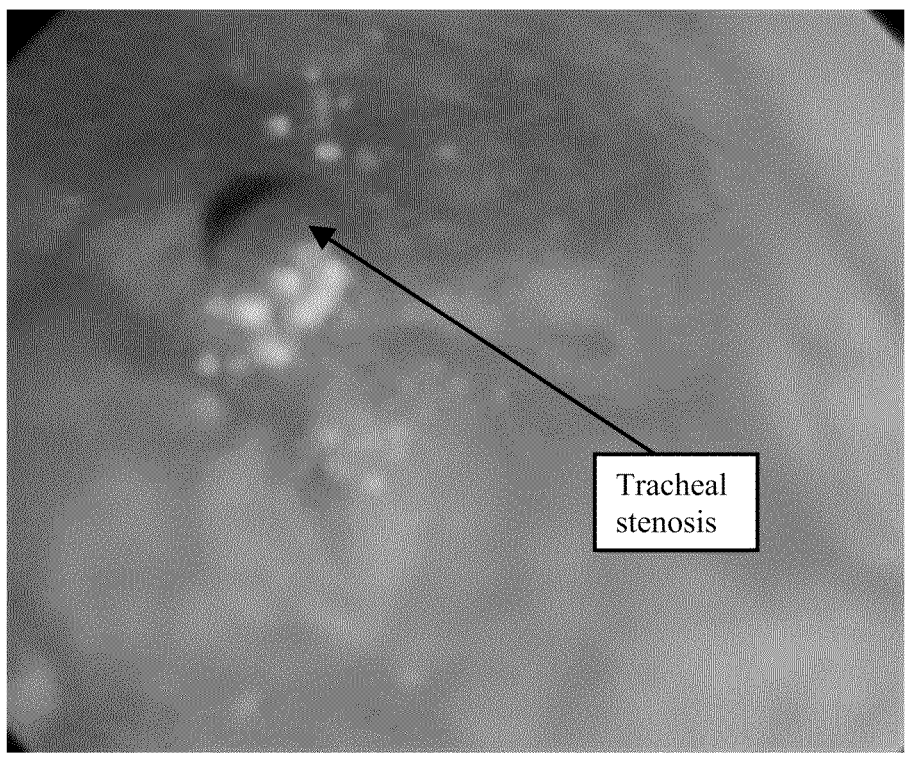
FIG. 8 shows a bronchoscopic interior view of tracheal-stenosis in 29 years old women with cervical trauma, according to an embodiment herein.

FIG. 7B shows a transmission electron microscopy (TEM) image of a nanocup with/or without growth factor. In FIG. 7B also shows the thick portion of the nano-cup.

According to one embodiment herein, an injectable matrix is fabricated to reconstruct some portions of the respiratory system. The respiratory system includes trachea and lungs. According to one embodiment herein, an injectable matrix can be fabricated to replace diseased or damaged portions of the trachea. The trachea is a cartilaginous and membranous-ringed tube where air passes to the lungs from the nose and mouth. Bio-artificial trachea which is formed after the injection of injectable matrix has similar architecture and mechanical properties to that of healthy trachea. Here the stem cells from blood circulatory systems migrates to the injection site and grow/differentiate into the tracheal cartilage. The bio-artificial structures can also be fabricated for tracheal epithelial tissues.

According to one embodiment herein, the injectable matrix, when used in a form of vapor and tested in two cases with severe bronchectasia and destructive lung disease, a candidate for lung transplantation can be fabricated to replace diseased or damaged portions of the lung, including a recent successful, first-in-man experience.

In humans, the trachea divides into the two main bronchi that enter the roots of the lungs. The bronchi then continue to divide within the lung and after multiple divisions give rise to bronchioles. The bronchial tree continues branching until it reaches the level of terminal bronchioles and lead to alveolar sacs. Alveolar sacs are made up of clusters of alveoli like individual grapes within a bunch. The individual alveoli are tightly wrapped in blood vessels and it is here that gas exchange actually occurs. According to the embodiments herein, all these structures of the air-conducting and alveolar portion can be formed by injectable matrix. The connective tissue and smooth muscle cells can be grown within the walls of the structure. The walls can also be lined with epithelial cells.

Once injectable matrix is injected to a damaged trachea (stenosis) that is dilated with holmium laser, the blood circulatory stem cells or stem cells derived from tissues or organs (tissue-specific progenitor cells) are immigrated into the injection site based on affinity of stem cell niches, growth factors and other physiological agents that release from cup-shaped nanoparticles and these stem cells differentiate into two main type of trachea structures i.e. cartilage and epithelium. The bio-artificial trachea can be fabricated to include similar architecture and mechanical properties to that of healthy trachea. For instance, the bio-artificial structure includes ring-like portions made from an injectable matrix. The blood circulatory stem cells or stem cells derived from tissues or organs (tissue-specific progenitor cells) are immigrated and differentiated based on affinity to stem cell niches and growth factors or other physiological agents that release from cup-shaped nanoparticles into the trachea cartilage tissues and epithelial tissues.

The embodiments herein relate to methods and injectable matrixes involving biocompatible structures for tissue engineering and organ replacement. The embodiments more specifically relate to methods and injectable matrixes involving biocompatible polymer with nanocup and stem cell niche formed by three-dimensional fabrication in target organ after injection for tissue engineering and organ replacement. After injection, the structures are three-dimensional and have a few microns in diameter and with the other structure of organ can mimic the shapes of micro architecture of the tissues and organs. Particles incorporating an additive can have various sizes; for example, particles may have a cross-sectional dimension of less than 1000 nm, less than 100 nm, less than 50 nm.

In some embodiments, the tissue specific progenitor cells or adult tissue-specific stem cells have the capacity to self-renew and generate functional differentiated cells that replenish lost cells throughout an organism's lifetime. The stem cell function is controlled by extracellular cues from the niche and by intrinsic genetic programs within the stem cell.

Injection of multiple matrixes with different volume and depth in target organ or tissue, along with effective mechanical stress increase the speed of the stem cells differentiation which are derived from blood circulatory stem cell or derived from tissue. This occurs when the stem cells are attached to specific niches of injected matrixes (enzymatic purified collagens with different concentration from target organ) and cause the slow release of growth factor from nanocup.

The biocompatible, biodegradable injectable matrix can comprise a composition to formulate a gel, paste, spray or vapor, nano and micro-particle, liquid or other injectable form. This injectable matrix is administered to the defect by injection. The number of injection related to type of tissue or organ structure. The complex organs such as the trachea involve more than one cell type so; the number of injections is more than one step. All of the structures such as scaffolds or injectable matrixes, niches, growth factors and other physiologic agents are special for desirable organs or tissues.

The dimension of each spherical matrix in the area of injection is generally from 0.02 mm to 1 cm (depending on volume of injection) in damaged (target) organ and tissue which specifically is 0.1 to 0.5 mm. The distance between each spherical matrix to another site of injection is approximately 0.1 to 1 cm and specifically is 0.5 to 1 mm 0.5 to 1 mm. The dimension and number of spherical matrix injection (depends on volume of injection) and number of injection per volume unit for each organ or tissue is different and nearly specific. The matrix in location of injection configures a network of spherical structure in the target organ (with or without internal or external mechanical support).

After the injection of matrix in the organ or tissue, the attachment of stem cells obtained from blood circulatory stem cells or stem cells derived from tissues or organs (tissue-specific progenitor cells) to injectable matrix occurs. In the next step, the co-relation of nearby organs along with the imposed stress would bring the proliferation and differentiation of cells in the target tissue or organs. In certain embodiments, the shaped polymeric injectable matrix construct has a circular shape or c-shape. In some embodiments, the shape of the polymeric injectable matrix construct is based on desired organ or tissue configuration.

Stem cell immigrate and attach to injected matrixes and after the release of growth factor(s), they differentiate into desirable target tissue or organ. Generally, differentiation occurs by two different procedures: firstly attachment of stem cells to specific niches and ultimate release of growth factor and other physiologic agents from nanocups, secondly, the mechanical and/or electrical stress on tissue or organ that may happen due to functional output of organ or due to the effect of near-by organs on target organ.

Advantage of using the injectable matrix described herein is the ability to create three dimensional matrix systems or networks with the site of injection as a physiologic organ and relationship with another organ and their properties to different stem cells and the replacement, regeneration, reconstruction, repair or a shaped to conform to at least a part of organs or tissues or regions. The injectable matrix described herein by can be combined either in different forms or combining different injectable matrix to make one or more forms.

An injectable matrix may also be injected into an organ by one or multi-steps

Experimental Section

A 29 year old female was having a 8.5 cm long tracheal destruction and stenosis which occurred 10 years back after trauma in a car accident. She was treated with APC laser during these years. CT, Radiologic and broncoscopic findings before this operational admission showed the stenosis started from two centimeters below the vocal cord and only 2-3 mm from tracheal lumen was opened and this stenosis continued to 2.5 cm until to tracheal bifurcation (about 8.5 cm).

After preparation and drape under general anesthesia fiberoptic broncoscopy (no. 6 mm) was passed through the upper part of trachea to detect exact location of stenosis. Rigid broncoscopy no. 4 through 6.5 was inserted orderly for dilatation and then laser probe was inserted into fibroptic bronchoscope for lasering the stenosis lumen. Meanwhile selected fibroptic portion, burnt (coagulated, cauterized) Upward by APC laser from 2 cm upper then bifurcation and all granulation tissue was removed.

Figure 9:
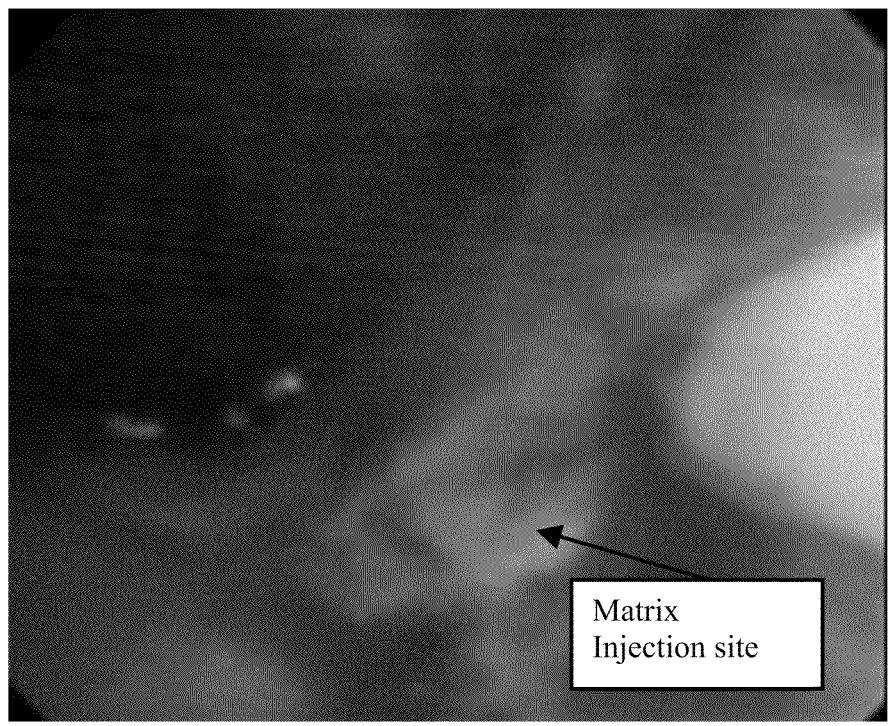
FIG. 9 shows a fiber-optic bronchoscopy of tracheal-stenosis showing the matrix injection site, according to an embodiment herein.

FIG. 9 shows a fiber-optic bronchoscopy of tracheal-stenosis showing the matrix injection site. The trachea was opened by APC laser, a needle was passed through and then a matrix injection was injected in the damaged sites.

A First-stage operation was done in January 2010 with specialized matrix injection by injection needle broncoscopy for 4.5 cm long trachea cartilage reconstruction. Amount of injectable matrix was 0.05-0.2 ml and distance between locations of injection was 0.1-1 mm apart. Injection depth was 2-3 mm and configuration of injections was C-shape or horseshoe shape (anatomic shape of cartilages of trachea). Second stage operation was done with specialized matrix injection for trachea epithelial reconstruction by injection needle of broncoscopy after 3 days. Amount of injectable matrix was 0.05-0.2 ml and locations of injection were 1 mm apart. Injection depth was 1-2 mm and configuration of injections was circle shape. In this site, procedures are complete. But in second part (proximal part, third stage operation was done with specialized matrix injection for the next 4 cm long trachea cartilage reconstruction as the same method after 1 month. Amount of injectable matrix was 0.05-0.2 ml and distance between locations of injection was 0.1-1 mm. Injection depth of matrix was 2-3 mm and configuration of injection was C-shape or horseshoe shape (generally, configuration of matrix injection is based on anatomical shape of desired organ). The next stage operation was done with specialized matrix injection for trachea epithelial reconstruction by injection needle of broncoscopy after 3 days. Amount of injectable matrix was 0.05-0.2 ml and locations of injection were 1 mm apart. Injection depth was 1-2 mm configuration of injection was circle shape.

Figure 10:
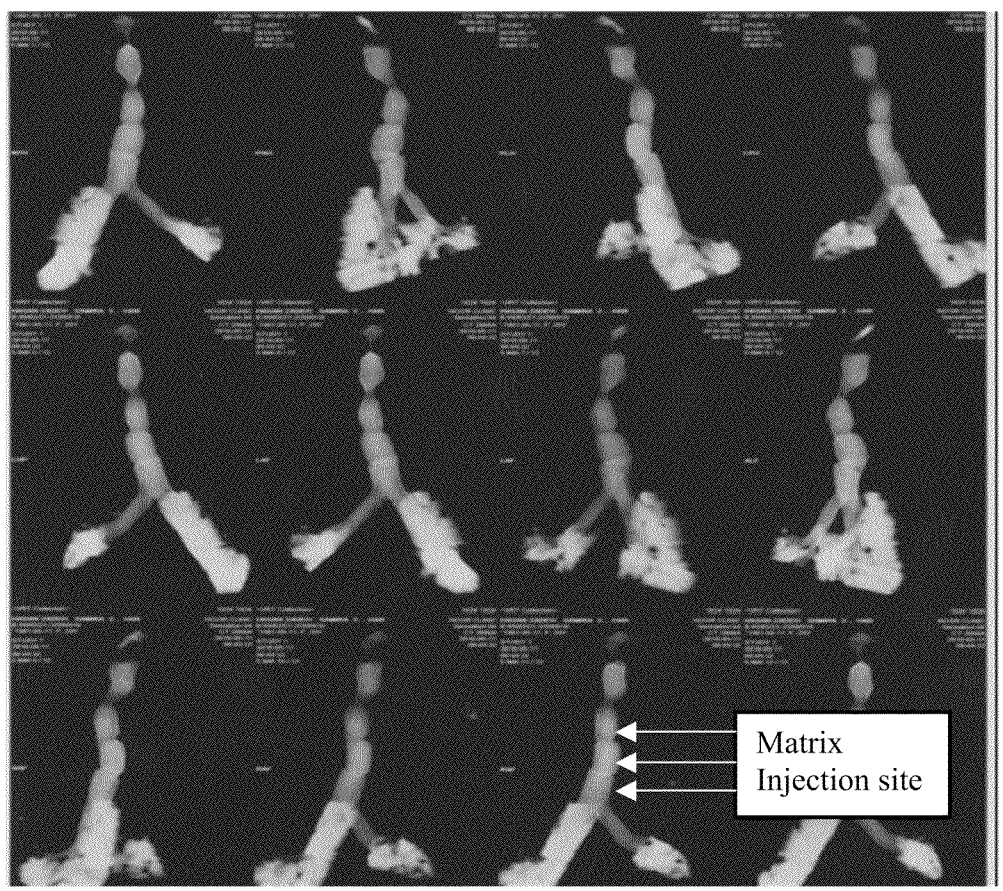
FIG. 10 shows a tracheal virtual CT-scan after one month of injection of injectable matrix in the trachea, according to an embodiment herein.
Figure 11:
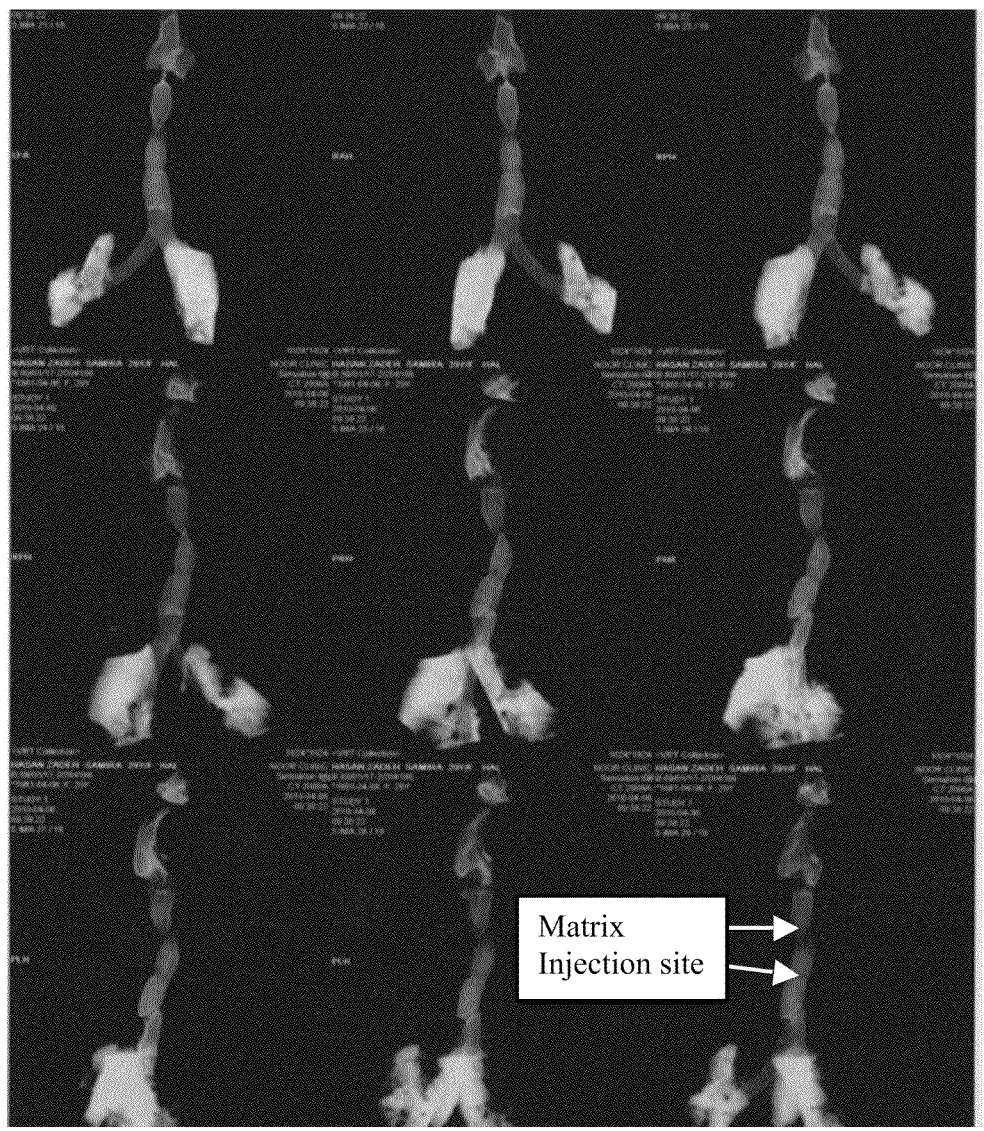
FIG. 11 shows a tracheal virtual CT-scan after two months of injection of injectable matrix in the trachea, according to an embodiment herein.

FIG. 10 shows a tracheal virtual CT-scan after one month of injection of injectable matrix in the trachea. According to FIG. 10, it can be seen that the trachea in the injection sites has normal shape.

Figure 12:
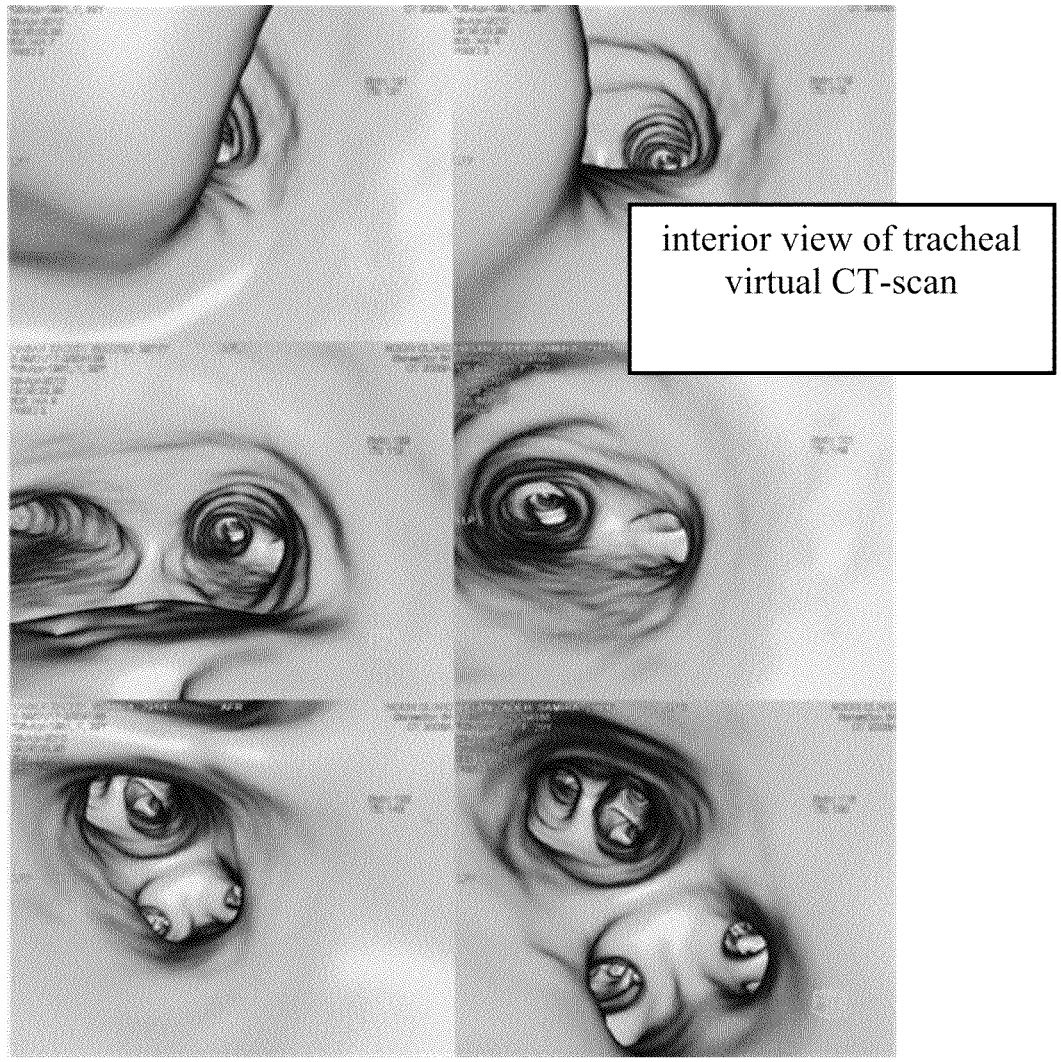
FIG. 12 shows an interior view of tracheal Virtual CT-scan after one month of injection of injectable matrix in the trachea, according to an embodiment herein.
Figure 13:
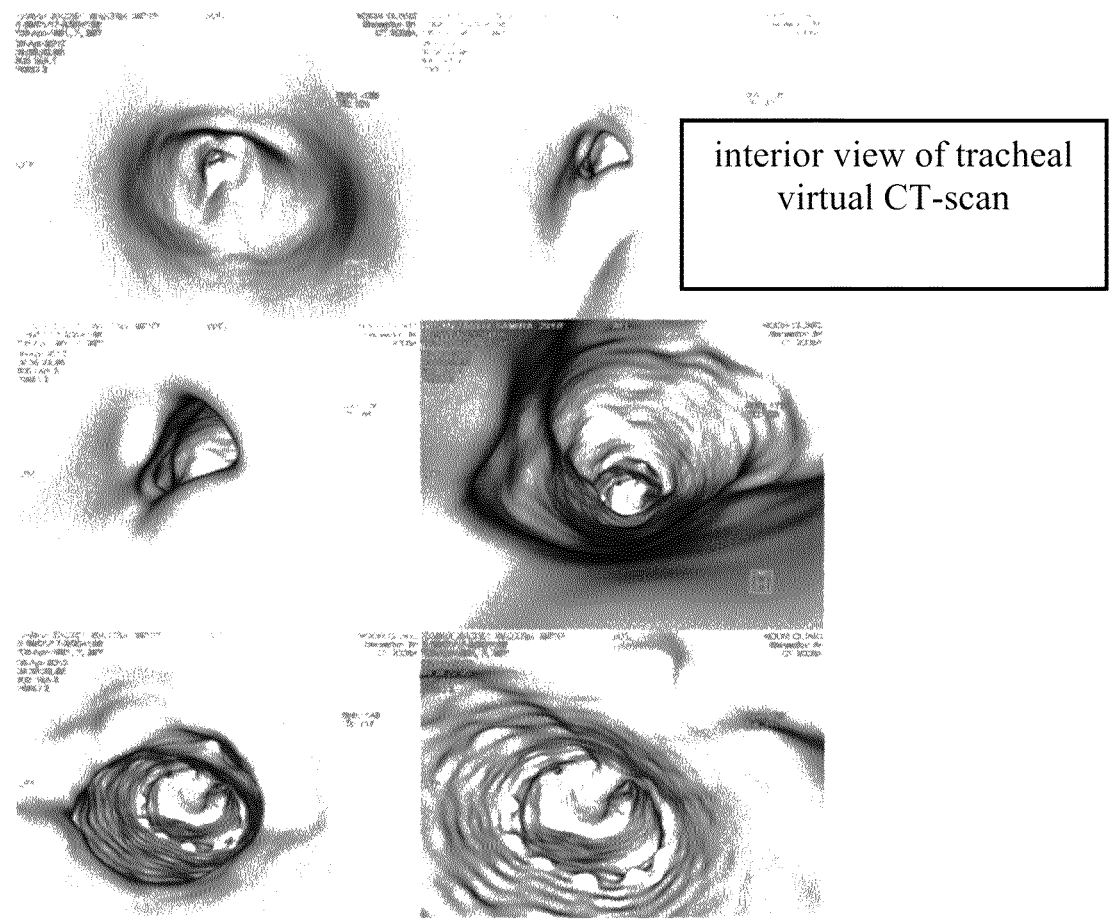
FIG. 13 shows an interior view of tracheal virtual CT-scan after one month of injection, according to an embodiment herein.

FIG. 12 shows an interior view of tracheal Virtual CT-scan after one month of injection of injectable matrix in the trachea. With respect to FIG. 12, it can be seen that the interior portion of the trachea in injection sites have approximately normal shape.

Figure 14:
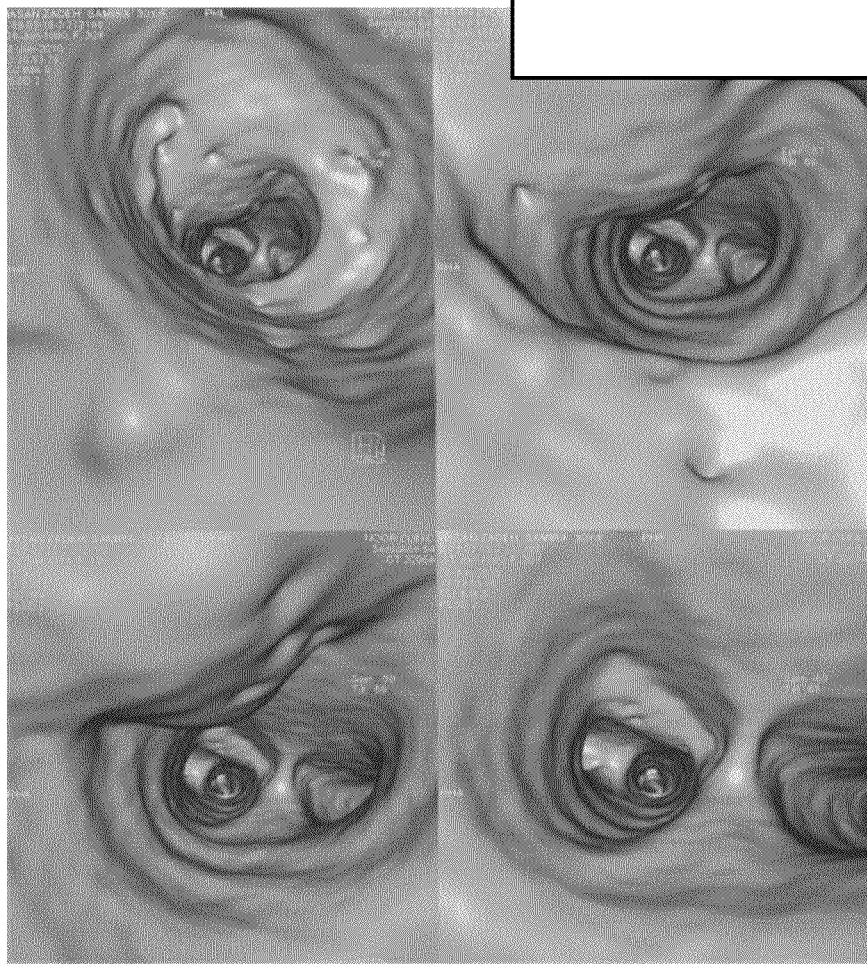
FIG. 14 shows an interior view of tracheal virtual CT-scan after three months of injection, according to an embodiment herein.
Figure 15:
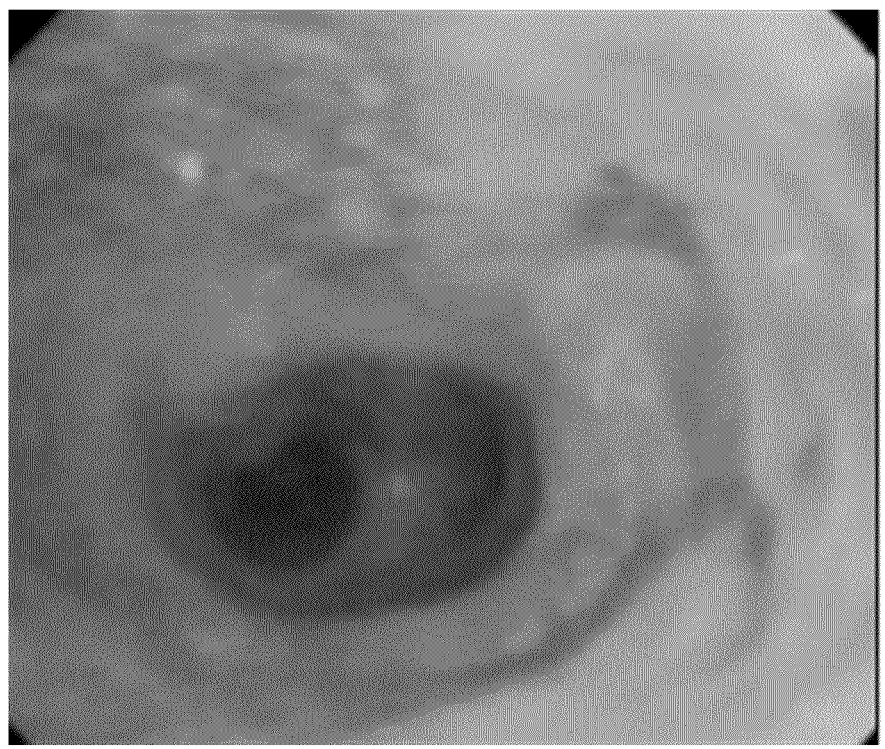
FIG. 15 shows an interior view of the tracheal bronchoscopy after four months of injection, according to an embodiment herein.

FIG. 14 shows an interior view of tracheal virtual CT-scan after three months of injection. With respect to FIG. 14, it can be seen that the interior portion of the trachea in the injection sites has completely normal shape.

At 3rd month of follow-up, virtual CT showed that bioartificial trachea became a part of recipient's trachea, in good position; its diameter was almost the same as the native trachea. Bronchoscopy demonstrated that upper and lower injected sites were normal, the inner side of native and bioartificial trachea was smooth with normal color. The diameter of bioartificial trachea was equal to patient's own trachea.

Figure 16:
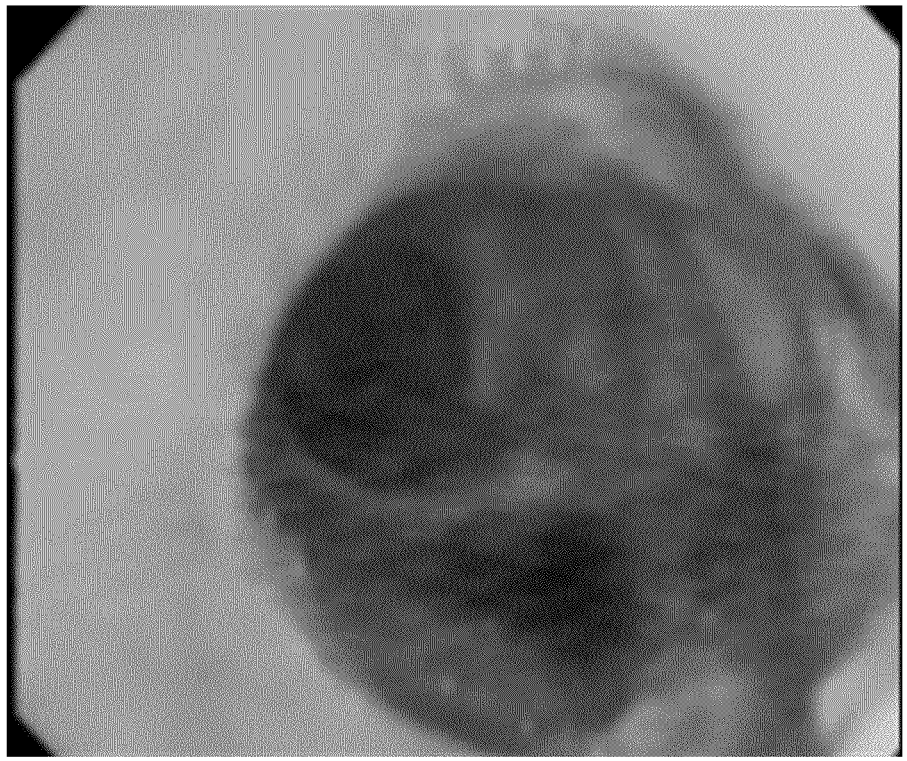
FIG. 16 shows an interior view of tracheal bronchoscopy after four months of injection of the injectable matrix, according to an embodiment herein.

FIG. 16 shows an interior view of tracheal bronchoscopy after four months of injection of the injectable matrix. With respect to FIG. 16, it can be seen that the interior portion of trachea in injection sites has completely normal shape. At 5th month follow-up, everything was normal; broncoscopy was the same as two months before.

Figure 17:
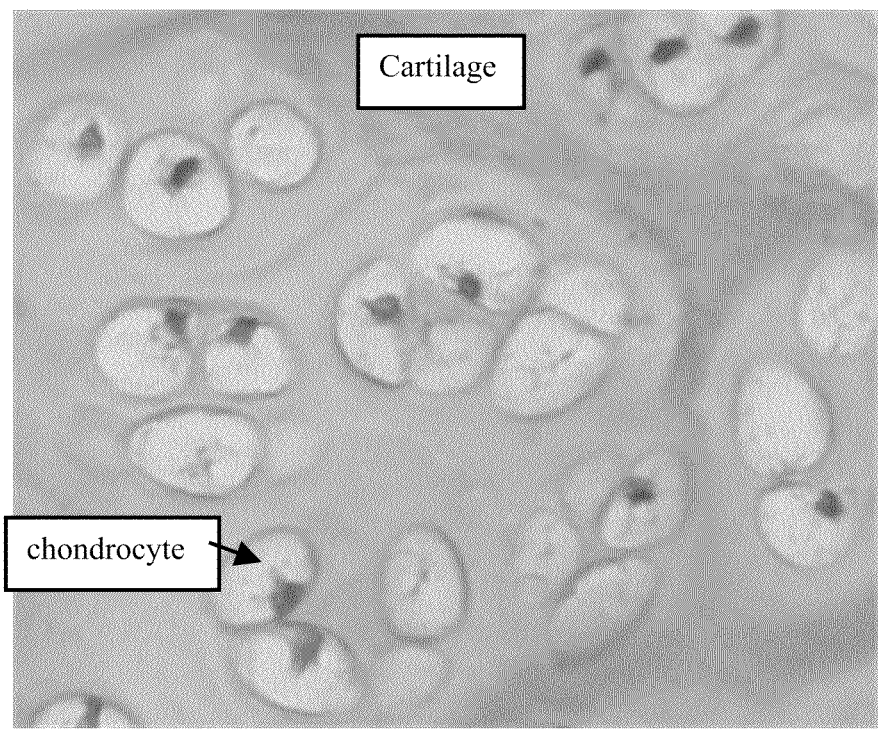
FIG. 17 shows a biopsy of the trachea cartilage after six months of injection of the injectable matrix, according to an embodiment herein.

FIG. 17 shows a biopsy of the trachea cartilage after six months of injection of the injectable matrix. At the 8th month after the operation, she lived totally a normal life.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method of tissue engineering for organ reconstruction comprising the steps of:
   injecting a matrix on or in an area of an organ or tissue in need of engineering or reconstruction,
   wherein the injectable matrix comprises a polymer and a stem cell niche comprising cup-shaped nanoparticles containing growth factors or physiological agents;
   permitting the creation of a three dimensional matrix system or network with the injected area of the organ or tissue as a whole matrix;
   allowing the migration of a plurality stem cells or tissue-specific progenitor cells to the three dimensional matrix system or network;
   wherein growth factors and physiological agents are released from the nanoparticles in the injected area of the organ or tissue; and
   permitting the proliferation and differentiation of the migrated plurality of stem cells or tissue-specific progenitor cells in the presence of a mechanical in-vivo stress;
   whereby the organ or tissue is constructed.

2. The method according to claim 1, wherein the injected matrix is in the form of a gel, a paste, a spray, a vapor of nano and micro-particle or liquid or in any other injectable form wherein the injected matrix is in the form of a hydrogel.

3. The method according to claim 1, wherein the plurality of stem cells is derived from blood circulatory system and tissue-specific progenitor cells of the organ or tissue.

4. The method according to claim 1, wherein the plurality of stem cells is differentiated based on affinity of the stem cell niche, the growth factors and physiologic agents and mechanical and electrical in-vivo stress.

5. The method according to claim 4, wherein the mechanical and electrical vivo stress depends on a function of the tissue or organ, a connection of the tissue or organ with adjacent organs or tissues and traction forces or shear stress based on function of the tissue or organ upon the complex of injectable matrix network and migrated stem cells.

6. The method according to claim 1, wherein the growth factor is selected from a group comprising of epidermal growth factor (EGF), transforming growth factor alpha (TGF-alpha), transforming growth factor beta (TGF-beta), fibroblast growth factor (FGF) and vascular epithelial growth factor (VEGF), wherein the fibroblast growth factor (FGF) is selected from a group consisting of bFGF, FGF2, FGF7, FGF 10 and any combination thereof.

7. The method according to claim 1, wherein the physiological agent is selected from a group comprising of biologically active molecules and wherein the biologically active molecules include peptides, steroid hormones, chemokines, cytokines or a combination thereof.

8. The method according to claim 1, wherein the organ or tissue is selected from a group comprising of structures involving hollow and epithelial organs and wherein the hollow and epithelial organs include respiratory organ, cardiovascular organ, gastrointestinal organ, lymphatic organ, dental organ, periodontal organ or skin organ.

9. The method according to claim 1, wherein the matrix injected into a complex organ is more than one and wherein the complex organ is trachea.

10. The method according to claim 1, wherein the matrix is injected without stem cells.

11. The method according to claim 1, wherein the matrix is injected in to one or more parts of the organ.

12. The method according to claim 1, wherein the injected matrix configures a network of spherical structure in the injected area of the tissue or organ.

13. An injectable matrix for tissue engineering or organ reconstruction comprising: a polymer; and
   a stem cell niche comprising cup-shaped nanoparticles containing growth factors or physiological agents.

14. The matrix according to claim 13, wherein the polymer is selected from a group comprising of synthetic polymers and natural polymers.

15. The matrix according to claim 14, wherein the synthetic polymer is selected from a group comprising of poly-caprolacton, poly-l-lysin, poly-lactic-co-glycolic acid.

16. The matrix according to claim 14, wherein the natural polymer is selected from a group comprising of collagen, elastin, chitosan, alginate or combination thereof and wherein the collagen includes 29 types of collagen and wherein the preferred type of collagen is I, II, III, IV and V.

17. The matrix according to claim 13, wherein the polymer is selected from a group comprising of fibronectin, laminin, glycoprotein, elastin, fibrillin, mucopolysaccharide, heparin sulfate, chondroitin sulfate, keratin sulfate, glycosaminoglycan, hyaluronic acid, proteoglycan, vitronectin, polysaccharide and any combination thereof.

18. The matrix according to claim 13, wherein the stem cell niche comprises a specified niche for specific organ wherein the specified niche comprises purified collagen from the organ.

19. The matrix according to claim 13, wherein the cup-shaped nanoparticles have diameter of less than 5 micrometer and wherein the cup-shaped nanoparticles have diameter of 60 to 1000 nm.

20. The matrix according to claim 13, wherein the growth factor is selected from a group comprising of epidermal growth factor (EGF), transforming growth factor alpha (TGF-alpha), transforming growth factor beta (TGF-beta), fibroblast growth factor (FGF) and vascular epithelial growth factor (VEGF), wherein the fibroblast growth factor (FGF) is selected from a group consisting of bFGF, FGF2, FGF7, FGF10 and any combination thereof.

21. The matrix according to claim 13, wherein the physiological agent is selected from a group comprising of biologically active molecules and wherein the biologically active molecules include peptides, steroid hormones, chemokines, cytokines or a combination thereof.

22. The matrix according to claim 13, wherein the shape of the matrix is to conform a shape of at least a part of organ or tissue.

* * * * *